US012620463B2

(12) United States Patent
     Khashman

(10) Patent No.: US 12,620,463 B2
(45) Date of Patent: *May 5, 2026

(54) SYSTEMS AND METHODS FOR AUTOMATED VALIDATION AND RESOLUTION OF EXCEPTION RECORDS

(71) Applicant: Technology Partners LLC, Charlotte, NC (US)

(72) Inventor: Sam Faris Khashman, Charlotte, NC (US)

(73) Assignee: Technology Partners LLC, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/354,316

(22) Filed: Oct. 9, 2025

(65) Prior Publication Data

US 2026/0038658 A1     Feb. 5, 2026

Related U.S. Application Data

(63) Continuation of application No. 18/940,976, filed on Nov. 8, 2024, now Pat. No. 12,462,910.

(60) Provisional application No. 63/547,984, filed on Nov. 9, 2023.

(51) Int. Cl.
    *G16H 10/60*     (2018.01)
    *G06F 9/451*     (2018.01)

(52) U.S. Cl.
    CPC ............. *G16H 10/60* (2018.01); *G06F 9/451* (2018.02)

(58) Field of Classification Search
    CPC ............................... G16H 10/60; G06F 9/451
    See application file for complete search history.

(56) References Cited

U.S. PATENT DOCUMENTS

| | | | | |
|---|---|---|---|---|
| 2007/0100659 A1* | 5/2007 | Preiss | .................... | G16H 10/20 705/2 |
| 2012/0029950 A1* | 2/2012 | Lyle | ....................... | G06Q 10/10 705/4 |
| 2016/0358284 A1* | 12/2016 | Bagley | .................... | G16H 10/60 |
| 2019/0065686 A1* | 2/2019 | Crane | .................... | G16H 10/60 |
| 2019/0325024 A1* | 10/2019 | Boone | .................. | G06F 40/226 |
| 2021/0375490 A1* | 12/2021 | Brown | .................. | G06Q 20/14 |

(Continued)

*Primary Examiner* — Fonya M Long
*Assistant Examiner* — Anthony Balaj
(74) *Attorney, Agent, or Firm* — Padowithz Alce; Quintin Scheitlin; Alce PLLC

(57) ABSTRACT

In some embodiments, a method for automated batch processing of a plurality of exception records includes displaying an automated batch processing graphical user interface comprising: a batch explorer user interface container that includes a hierarchical view of a plurality of exception record batches, a first artifact user interface component that is configured to display a plurality of top-level exception records associated with an exception record batch selected in the batch explorer user interface element, a second artifact user interface component that is configured to display a plurality of sub-level exception records subordinate to a top-level exception record selected in the first artifact user interface component, and a plurality of editable user interface fields that are configured to receive input for modifying a plurality of attributes associated with a sub-level exception record selected in the second artifact user interface component.

20 Claims, 14 Drawing Sheets

(56) References Cited

U.S. PATENT DOCUMENTS

2023/0207080 A1* 6/2023 Willis ................. G06F 21/6245
                                                    705/3
2023/0317260 A1* 10/2023 Zahora .............. G06Q 10/0639
                                                    705/3

* cited by examiner

150

100

Record Exception Identification Module 160

Record Processing and Release Module 170

Automated Validation Module 180

Automated Posting Module 190

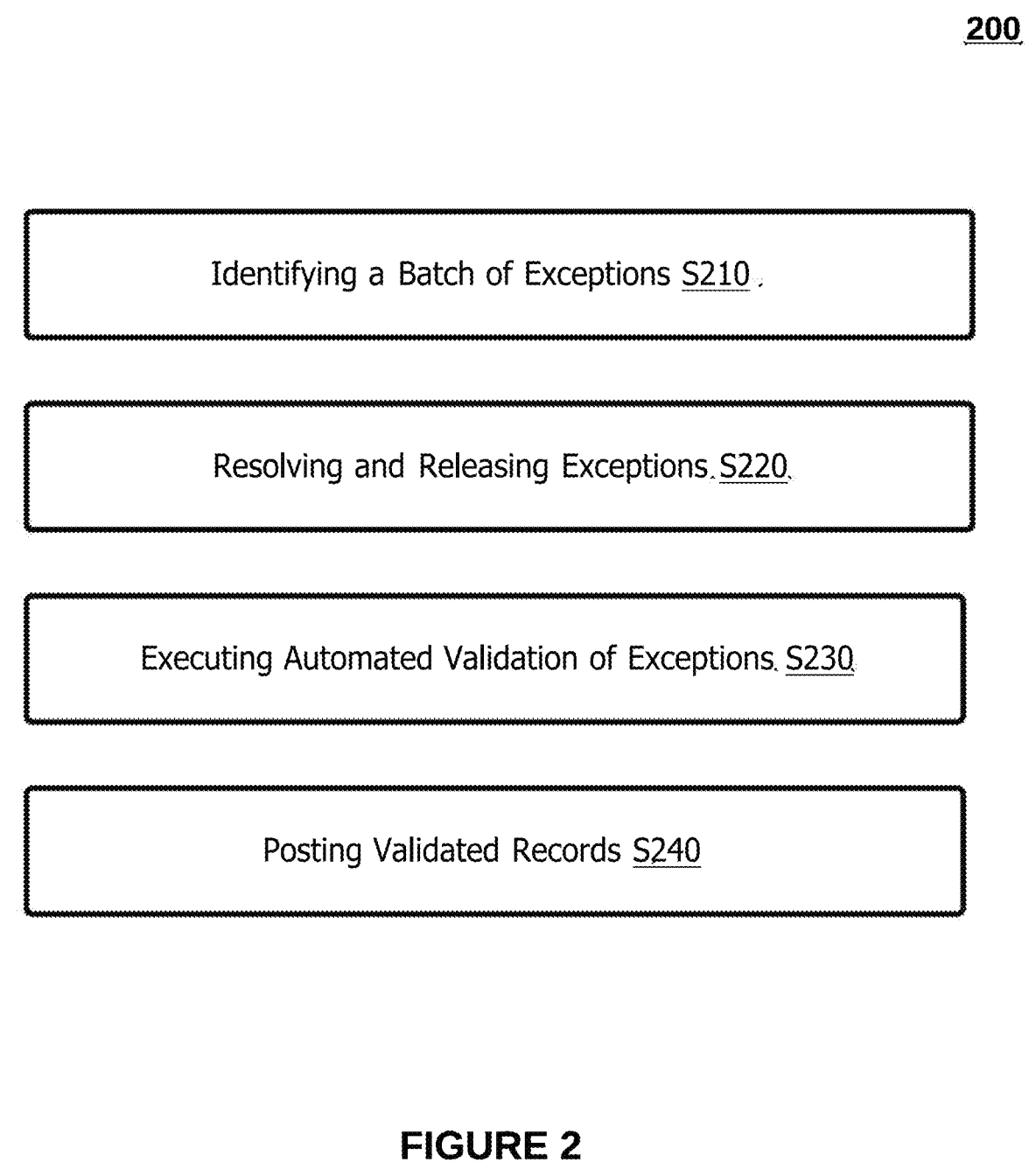

200

Identifying a Batch of Exceptions S210

Resolving and Releasing Exceptions S220

Executing Automated Validation of Exceptions S230

Posting Validated Records S240

FIGURE 2

Imagine - (ANESTHESIA DEMO) v23.0.03 - Logged in as: DTeam - [ChargeCentral]

Performance Manager   Help

7 Patients

| Last Name | SSN | Address | Address 2 | City | State |
|---|---|---|---|---|---|
| PALMER | | 8757 Red Oak Blvd | PO BOX 100 | Charlotte | NC |
| HARRISON | 000-26-6060 | 8757 Red Oak Blvd | PO BOX 100 | Charlotte | NC |
| ORTIZ | 020-68-0880 | 8757 Red Oak Blvd | PO BOX 100 | Charlotte | NC |
| WELLS | 002-06-0000 | 8757 Red Oak Blvd | PO BOX 100 | Charlotte | NC |
| GORDON | | 8757 Red Oak Blvd | PO BOX 100 | Charlotte | NC |
| HOLMES | 000-62-0060 | 8757 Red Oak Blvd | PO BOX 100 | Charlotte | NC |
| HUNT | 000-02-0822 | 8757 Red Oak Blvd | PO BOX 100 | Charlotte | NC |

2 Visits

| Patient DOB | Visit Number | Location | Visit Date | History Number | Referring Doctor |
|---|---|---|---|---|---|
| 7/24/1966 | 000011640 | 1. First Location | 7/16/2013 | 003796 | 2 - JOHNSON.JO |
| 7/24/1966 | 000011629 | 1. First Location | 7/16/2013 | 003796 | |

1 Charge

| Visit Number | Location | Post Date | Date Of Service | Procedure |
|---|---|---|---|---|
| 000011640 | 1 - First Location | 7/16/2013 | 7/16/2013 | 43580 - REVJ GASTRODUOL ANAST W/RCNS |

III

| Oth. Doctor | 0 | ··· |
|---|---|---|
| 0 ··· | 0 ··· | + |
| 0 ··· | 0 ··· | + |

| Zip | Zip 2 | Phone Number | DOB | Gender | Resp Party First Name | Resp Party Middle Name |
|-----|-------|--------------|-----|--------|----------------------|------------------------|
| 28217 | | (704)553-1004 | 07/24/1966 | M | JEROME | E |
| 28217 | | (704)553-1004 | 05/24/1933 | F | MARGARET | E |
| 28217 | | (704)553-1004 | 02/16/1978 | M | RUSSELL | G |
| 28217 | | (704)553-1004 | 09/07/1960 | M | CHRISTOPHER | |
| 28217 | | (704)553-1004 | 05/30/1974 | M | JOHN | K |
| 28217 | | (704)553-1004 | 09/28/1966 | F | AMY | E |
| 28217 | | (704)553-1004 | 07/13/1928 | M | LLOYD | E |

. . . . .

| Primary Insurance | Secondary Insurance | Tertiary Insurance |
|-------------------|---------------------|--------------------|
| | | |

| | Billing Procedure | Modifier | Units | Order Number |
|---|-------------------|----------|-------|--------------|
| | 00790 - ANES IPRUPR | 34 | 1 | |

FIG. 3(Cont...)

| Resp Party Last Name | Resp Party Address |
|---|---|
| PALMER | 8757 Red Oak Blv |
| HARRISON | |
| ORTIZ | 8757 Red Oak Blv |
| WELLS | 8757 Red Oak Blv |
| GORDON | 8757 Red Oak Blv |
| HOLMES | 8757 Red Oak Blv |
| HUNT | 8757 Red Oak Blv |

Filter (None) ▾ Options ▾

| Created Date | |
|---|---|
| 6/13/2018 | |
| 6/13/2018 | |

Filter (None) ▾ Options ▾

| Diagnosis Code 1 | Diagnosis Code 2 | Diagnosis Code 3 | |
|---|---|---|---|
| 337.22 | 71947 | 729.1 | |

Options ▴

Action ▴

Go To ▴

Release

Refresh

Save

Close

FIG. 3(Cont...)

Imagine - (ANESTHESIA DEMO) v23.0.03 - Logged in as: DTeam - [ChargeCentral]

Dashboard    Performance Manager    Help

1 Patients

| Middle Name | Last Name | SSN | Address | Address 2 | City | State |
|---|---|---|---|---|---|---|
| | HERNANDEZ | 000-02-0000 | 8757 Red Oak Blvd | PO BOX 100 | Charlotte | NC |

| Patient DOB | Visit Number | Location | Visit Date | History Number |
|---|---|---|---|---|
| 7/30/1939 | 000011552 | 1 . First Location | 7/15/2013 | 005058 |

| Visit Number | Location | Post Date | Date Of Service | Procedure |
|---|---|---|---|---|
| 000011552 | 1 - First Location | 7/15/2013 | 7/15/2013 | 99213 - OFFICE OUTPTEST15 MIN |

Oth. Doctor

ⓘ Validation Failed
Batch Number:        01112017120020_DL
Bucket:              (None)
On Hold:             NO
Hold Note:
Patient:             HERNANDEZ. RICARDO
Visit Number:        000011552
Location:            1 - First Location
Exempt:              False
Override Bass Units: Override

FIG. 4(Cont...)

| Zip | Zip 2 | Phone Number | DOB | Gender | Resp Party First Name |
|---|---|---|---|---|---|
| 28217 | | (704)553-1004 | 07/30/1939 | M | RICARDO |

2 Visits

| Referring Doctor | Primary Insurance | Secondary Insurance | Tertiary Insurance |
|---|---|---|---|
| 34 - SCOTT . STEP | 69 - MUTUAL OF O | | |

1 Charge

| | Billing Procedure | Modifier | Units | Order Number |
|---|---|---|---|---|
| | | P1 | 1 | 99999 |

| | |
|---|---|
| Prim Insurance: | 69 - MURUAL OF OMAHA |
| Sec. Insurance: | |
| Tert. Insurance: | |
| Place of Service: | OFC |
| Service Dates: | 7/15/2013 |
| Procedure: | 99213 - OFFICE OUTPUT EST15 MIN |
| Charge Fee: | |
| Doctor: | 2 |
| Ref. Doctor: | 1 . SMITH. JAMES A |

FIG. 4(Cont...)

| Resp Party Middle Name | Resp Party Last Name | Resp Party Address |
|---|---|---|
| | HERNANDEZ | 8757 Red Oak Blvd |

Filter (None) ▾ Options ▾

| Created Date |
|---|
| 6/13/2018 |

Filter (None) ▾ Options ▾

| Diagnosis Code 1 | Diagnosis Code 2 | Diagnosis Code 3 | |
|---|---|---|---|
| 721 3 | 724 02 | 338.29 | 722 |

Options ▲

Action ▲

Go To ▲

Release

Refresh

Save

Close

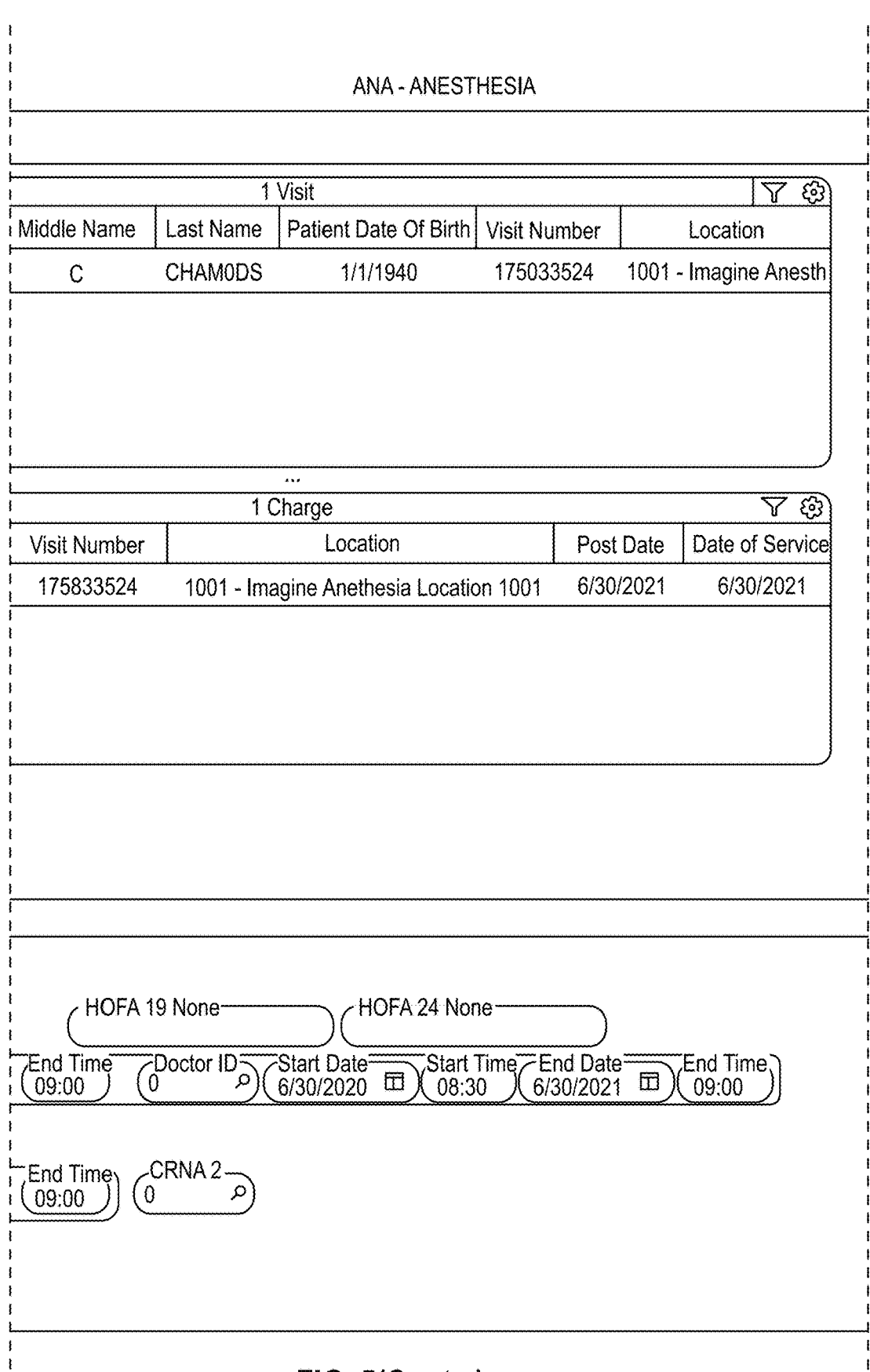
FIG. 5(Cont...)

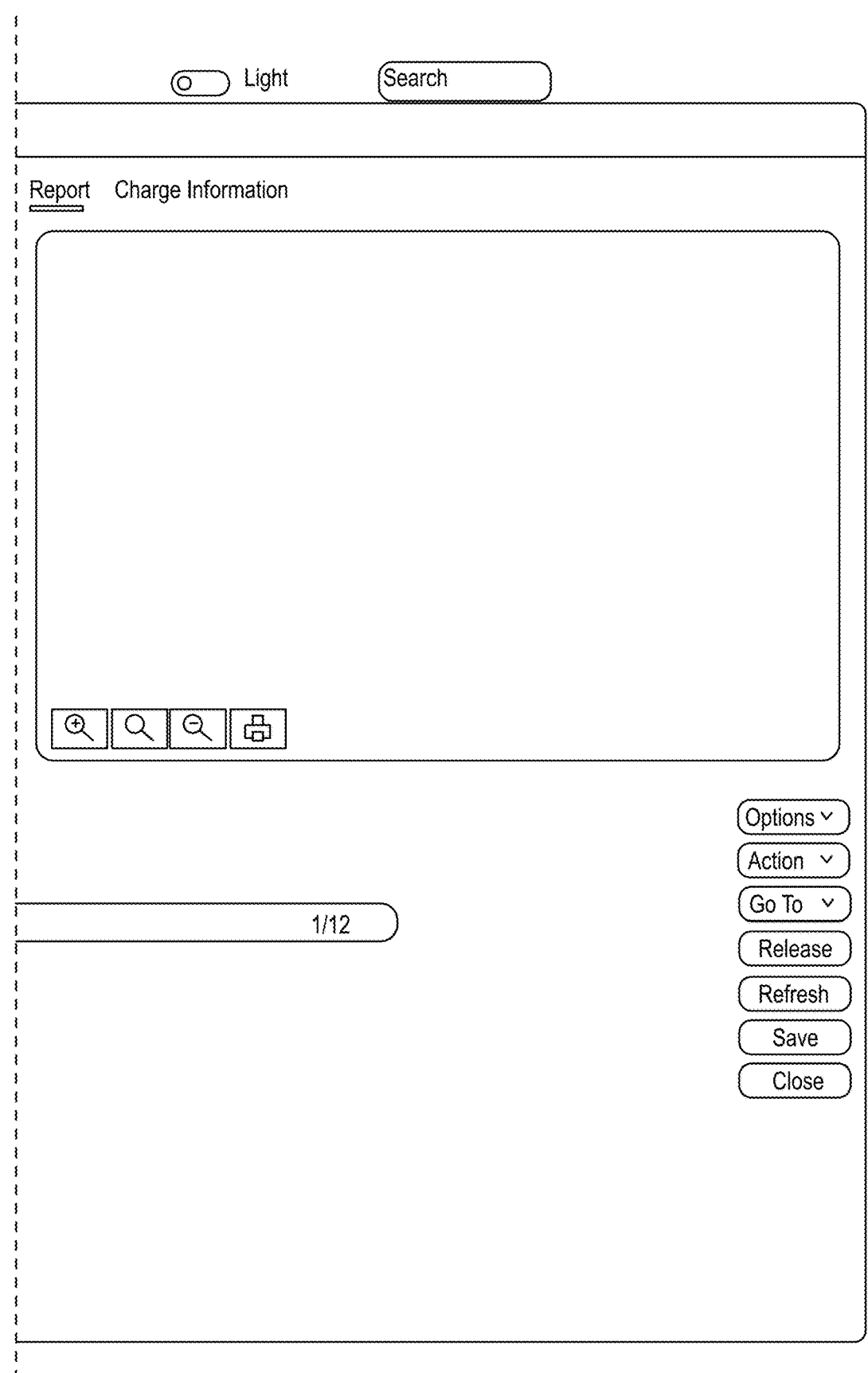
FIG. 5(Cont...)

SYSTEMS AND METHODS FOR AUTOMATED VALIDATION AND RESOLUTION OF EXCEPTION RECORDS

CROSS-REFERENCE TO RELATED APPLICATIONS

This application is a continuation of U.S. patent application Ser. No. 18/940,976, filed on 8 Nov. 2024, which claims the benefit of U.S. Provisional Application No. 63/547,984, filed 9 Nov. 2023, which is incorporated in its entirety by this reference.

TECHNICAL FIELD

This invention relates generally to the exception management field and, more specifically, to new and useful systems, methods, and user interfaces for automated validation and resolution of exception records.

BACKGROUND

Healthcare providers, particularly in specialized fields such as anesthesia, are typically tasked with addressing numerous exception records that require intra-record validation on a daily basis. This process focuses on validating individual records for inconsistencies or errors within their own data fields, such as discrepancies in procedure times, missing or incorrect codes, or provider information. However, these intra-record errors often have broader implications that can affect other records. For instance, an error in the scheduling or assignment of a provider within one record may result in time conflicts with other records, creating a need for further adjustments.

While intra-record validation ensures the accuracy of data within a single record, its impact may extend across multiple records by raising conflicts, such as overlapping schedules or inconsistent provider assignments. The manual process of reviewing and correcting these records is not only time-consuming but also prone to errors, particularly when the issues span across related records.

Accordingly, there is a need for new and improved systems, methods, and user interfaces that automate intra-record validation while mitigating its potential cross-record effects. The embodiments of the present application provide technical solutions that at least address the needs described above, as well as the deficiencies of the state of the art.

BRIEF SUMMARY OF THE INVENTION(S)

In some embodiments, a method for automated batch processing of a plurality of exception records includes displaying an automated batch processing graphical user interface comprising: a batch explorer user interface container that includes a hierarchical view of a plurality of exception record batches, a first artifact user interface component that is configured to display a plurality of top-level exception records associated with an exception record batch selected in the batch explorer user interface element, a second artifact user interface component that is configured to display a plurality of sub-level exception records subordinate to a top-level exception record selected in the first artifact user interface component, and a plurality of editable user interface fields that are configured to receive input for modifying a plurality of attributes associated with a sub-level exception record selected in the second artifact user interface component; receiving, via the plurality of editable user interface fields, one or more inputs for intra-record resolution of an attribute exception associated with one or more attributes of the plurality of attributes associated with the sub-level exception record; and automatically executing a plurality of inter-record validations for the exception record batch after receiving the one or more inputs, wherein automatically executing the plurality of inter-record validations includes: (I) automatically detecting, via an inter-record time concurrency validation, that one or more groups of top-level exception records and sub-level exception records of the exception record batch is associated with a time concurrency validation error, (II) automatically re-positioning the one or more groups of top-level exception records and sub-level exception records associated with the time concurrency validation error into a time concurrency review queue of the batch explorer user interface element based on the automatically detecting of (I), (III) automatically detecting, via an inter-record modifier validation, that one or more groups of top-level exception records and sub-level exception records of the exception record batch is associated with a modifier processing validation error, and (IV) automatically re-positioning the one or more groups of top-level exception records and the sub-level exception records associated with the modifier processing validation error into a modifier processing review queue of the batch explorer user interface element based on the automatically detecting of (III).

In some embodiments, the method further comprises after re-positioning the one or more groups of top-level exception records and sub-level exception records into the time concurrency review queue: receiving, via the automated batch processing graphical user interface, one or more inputs for resolving the time concurrency validation error associated with the one or more groups of top-level exception records and sub-level exception records, and in response to receiving the one or more inputs for resolving the time concurrency validation error: ceasing display of the one or more groups of top-level exception records and sub-level exception records previously associated with the time concurrency validation error in the time concurrency review queue; and automatically executing the inter-record modifier validation after resolving the time concurrency validation error.

In some embodiments, the time concurrency validation error is caused by a violation of a value of an attribute being concurrently assigned to more than a pre-defined number of sub-level exception records during a respective time interval, and the one or more inputs for resolving the time concurrency validation error modifies the value of the attribute across the sub-level exception records to satisfy the pre-defined number.

In some embodiments, the method further comprises after re-positioning the one or more groups of top-level exception records and sub-level exception records into the modifier processing review queue: receiving, via the automated batch processing graphical user interface, one or more inputs for resolving the modifier processing validation error associated with the one or more groups of top-level exception records and sub-level exception records, and in response to receiving the one or more inputs for resolving the modifier processing validation error: ceasing display of the one or more groups of top-level exception records and sub-level exception records previously associated with the modifier processing validation error in the modifier processing review queue; and converting the one or more groups of top-level exception records and sub-level exception records previously associated with the modifier processing validation error to one or more groups of top-level and sub-level validated records; and automatically moving the one or more groups of top-level and sub-level validated records into a post-validated records queue for transmitting to one or more corresponding user accounts.

In some embodiments, the modifier processing validation error is caused by a violation of a modifier attribute applied to one or more sub-level exception records that conflicts with predefined modifier rules.

In some embodiments, the attribute exception associated with the one or more attributes includes a respective attribute of the one or more attributes having an incorrect value, the one or more inputs for intra-record resolution of the attribute exception include an input for the respective attribute from having the incorrect value to having a correct value, and the plurality of inter-record validations determines if changing the respective attribute to the correct value results in any cascading validation errors across other top-level exception records or other sub-level exception records of the exception record batch.

In some embodiments, the batch explorer user interface container includes a plurality of service period entries, and a respective service period entry of the plurality of service period entries includes one or more batch node entries that corresponds to one or more exception record batches associated with the respective service period entry, including a first batch node entry corresponding to the exception record batch; and the first batch node entry that corresponds to the exception record batch includes a plurality of sub-elements, including: a first sub-element that is selectable to display one or more groups of top-level exception records and sub-level exception records that are associated with the exception record batch; a second sub-element that is selectable to display the time concurrency review queue, wherein the time concurrency review queue is configured to present the one or more groups of top-level exception records and sub-level exception records that are associated with the time concurrency validation error; a third sub-element that is selectable to display the modifier processing review queue, wherein the modifier processing review queue is configured to present the one or more groups of top-level exception records and sub-level exception records that are associated with modifier processing validation error; and a fourth sub-element that is selectable to display a post-validated records queue, wherein the post-validated records queue is configured to display one or more groups of top-level and sub-level validated records that are no longer associated with the time concurrency validation error and the modifier processing validation error.

In some embodiments, the sub-level exception record corresponds to an unreleased sub-level exception record, a respective editable user interface field is visually emphasized to indicate that a value of a respective attribute of the plurality of attributes relates to the attribute exception, the one or more inputs include a first input for changing the value of the respective attribute to a new value that resolves the attribute exception. In some embodiments, the method further comprises: receiving, via the automated batch processing graphical user interface, a second input for releasing the unreleased sub-level exception record with the new value for the respective attribute, and based on receiving the first input and the second input: converting, in a computer database, the unreleased sub-level exception record to a released sub-level exception record; determining if the exception record batch includes another unreleased sub-level exception record; and if the determining determines that the exception record batch does include another unreleased sub-level exception record: automatically executing the plurality of inter-record validations for the exception record batch.

In some embodiments, the method further comprises: based on receiving the first input and the second input: if the determining determines that the exception record batch does include another unreleased sub-level exception record: forgoing automatically executing the plurality of inter-record validations for the exception record batch until the exception record batch does not include another unreleased sub-level exception record.

In some embodiments, a respective editable user interface field of the plurality of editable user interface elements: corresponds to a respective attribute of the plurality of attributes associated with the sub-level exception record, includes a value of the respective attribute in the sub-level exception record, and is visually emphasized to indicate that the value of the respective attribute relates to an exception.

In some embodiments, a first sub-level exception record of the plurality of sub-level exception records corresponds to the sub-level exception record selected in the second artifact user interface component. In some embodiments, the method further comprises: receiving an input for changing the sub-level exception record selected in the second artifact user interface component from the first sub-level exception record to a second sub-level exception record of the plurality of sub-level exception records; and updating the plurality of editable user interface fields from modifying the plurality of attributes associated with the first sub-level exception record to modifying the plurality of attributes associated with the second sub-level exception record.

In some embodiments, when the sub-level exception record selected in the second artifact user interface component corresponds to the first sub-level exception record, the plurality of editable user interface fields display values of the plurality of attributes associated with the first sub-level exception record; and when the sub-level exception record selected in the second artifact user interface component corresponds to the second sub-level exception record, the plurality of editable user interface fields display values of the plurality of attributes associated with the second sub-level exception record.

In some embodiments, the automated batch processing graphical user interface includes an upper section and a lower section; and the upper section of the automated batch processing graphical user interface includes: the batch explorer user interface container positioned on a left side of the upper section, wherein the batch explorer user interface container substantially spans 20% of a width of the upper section, the first artifact user interface component positioned on a right side of the upper section, wherein the first artifact user interface component substantially spans 80% of the width of the upper section, and the second artifact user interface component positioned on the right side of the upper section and below the first artifact user interface component, wherein the first artifact user interface component substantially spans 80% of the width of the upper section; and the lower section of the automated batch processing graphical user interface includes: the plurality of editable user interface fields that are configured to receive the input for modifying the plurality of attributes associated with the sub-level exception record selected in the second artifact user interface component, wherein the plurality of editable user interface fields substantially spans 100% of a width of the lower section.

In some embodiments, the method further comprises receiving, via the batch explorer user interface container, an input selecting a batch node entry corresponding to the exception record batch; and based on receiving the input selecting the batch node entry: obtaining, from a computer database, the plurality of top-level exception records associated with the exception record batch; and displaying the plurality of top-level exception records in the first artifact user interface component based on the obtaining of the plurality of top-level exception records; receiving, via the first artifact user interface component, a second input selecting an entry corresponding to the top-level exception record of the plurality of top-level exception records; and based on receiving the second input: obtaining, from the computer database, the plurality of sub-level exception records subordinate to the top-level exception record; and displaying the plurality of sub-level exception records in the second artifact user interface component based on the obtaining of the plurality of sub-level exception records.

In some embodiments, the hierarchical view of the plurality of exception record batches includes: a root node entry that represents an aggregation of the plurality of exception record batches, a batch node entry that is subordinate to the root node entry and corresponds to the exception record batch of the plurality of exception record batches, and a plurality of additional batch node entries that correspond to other exception record batches in the plurality of exception record batches.

In some embodiments, the batch node entry corresponding to the exception record batch includes text that indicates: a service date associated with the exception record batch, and a total number of sub-level exceptions subordinate to the plurality of top-level exception records.

In some embodiments a first top-level exception record of the plurality of top-level exception records corresponds to the top-level exception record selected in the second artifact user interface component. In some embodiments, the method further comprises: receiving an input for changing the top-level exception record selected in the first artifact user interface component from the first top-level exception record to a second top-level exception record of the plurality of top-level exception records; and updating the second artifact user interface component from displaying the plurality of sub-level exception records subordinate to the first top-level exception record to displaying a plurality of sub-level exception records subordinate to the second top-level exception record.

In some embodiments, a computer-program product comprises a non-transitory machine-readable storage medium storing computer instructions that, when executed by one or more processors, perform operations comprising: displaying an automated batch processing graphical user interface comprising: a batch explorer user interface container that includes a hierarchical view of a plurality of exception record batches, a first artifact user interface component that is configured to display a plurality of top-level exception records associated with an exception record batch selected in the batch explorer user interface element, a second artifact user interface component that is configured to display a plurality of sub-level exception records subordinate to a top-level exception record selected in the first artifact user interface component, and a plurality of editable user interface fields that are configured to receive input for modifying a plurality of attributes associated with a sub-level exception record selected in the second artifact user interface component; receiving, via the plurality of editable user interface fields, one or more inputs for intra-record resolution of an attribute exception associated with one or more attributes of the plurality of attributes associated with the sub-level exception record; and automatically executing a plurality of inter-record validations for the exception record batch after receiving the one or more inputs, wherein automatically executing the plurality of inter-record validations includes: (I) automatically detecting, via an inter-record time concurrency validation, that one or more groups of top-level exception records and sub-level exception records of the exception record batch is associated with a time concurrency validation error, (II) automatically re-positioning the one or more groups of top-level exception records and sub-level exception records associated with the time concurrency validation error into a time concurrency review queue of the batch explorer user interface element based on the automatically detecting of (I), (III) automatically detecting, via an inter-record modifier validation, that one or more groups of top-level exception records and sub-level exception records of the exception record batch is associated with a modifier processing validation error, and (IV) automatically re-positioning the one or more groups of top-level exception records and the sub-level exception records associated with the modifier processing validation error into a modifier processing review queue of the batch explorer user interface element based on the automatically detecting of (III).

In some embodiments, a computer-implemented system comprises: one or more processors; a memory; and a computer-readable medium operably coupled to the one or more processors, the computer-readable medium having computer-readable instructions stored thereon that, when executed by the one or more processors, cause a computing device to perform operations comprising: displaying an automated batch processing graphical user interface comprising: a batch explorer user interface container that includes a hierarchical view of a plurality of exception record batches, a first artifact user interface component that is configured to display a plurality of top-level exception records associated with an exception record batch selected in the batch explorer user interface element, a second artifact user interface component that is configured to display a plurality of sub-level exception records subordinate to a top-level exception record selected in the first artifact user interface component, and a plurality of editable user interface fields that are configured to receive input for modifying a plurality of attributes associated with a sub-level exception record selected in the second artifact user interface component; receiving, via the plurality of editable user interface fields, one or more inputs for intra-record resolution of an attribute exception associated with one or more attributes of the plurality of attributes associated with the sub-level exception record; and automatically executing a plurality of inter-record validations for the exception record batch after receiving the one or more inputs, wherein automatically executing the plurality of inter-record validations includes: (I) automatically detecting, via an inter-record time concurrency validation, that one or more groups of top-level exception records and sub-level exception records of the exception record batch is associated with a time concurrency validation error, (II) automatically re-positioning the one or more groups of top-level exception records and sub-level exception records associated with the time concurrency validation error into a time concurrency review queue of the batch explorer user interface element based on the automatically detecting of (I), (III) automatically detecting, via an inter-record modifier validation, that one or more groups of top-level exception records and sub-level exception records of the exception record batch is associated with a modifier processing validation error, and (IV) automatically re-positioning the one or more groups of top-level exception records and the sub-level exception records associated with the modifier processing validation error into a modifier processing review queue of the batch explorer user interface element based on the automatically detecting of (III).

In some embodiments, the hierarchical view of the plurality of exception record batches includes: a root node entry that represents an aggregation of the plurality of exception record batches, a batch node entry that is subordinate to the root node entry and corresponds to the exception record batch of the plurality of exception record batches, and a plurality of additional batch node entries that correspond to other exception record batches in the plurality of exception record batches.

BRIEF DESCRIPTION OF THE FIGURES

FIG. 2 illustrates an example method 200 in accordance with one or more embodiments of the present application.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Medical Data Processing System

Figure 1:
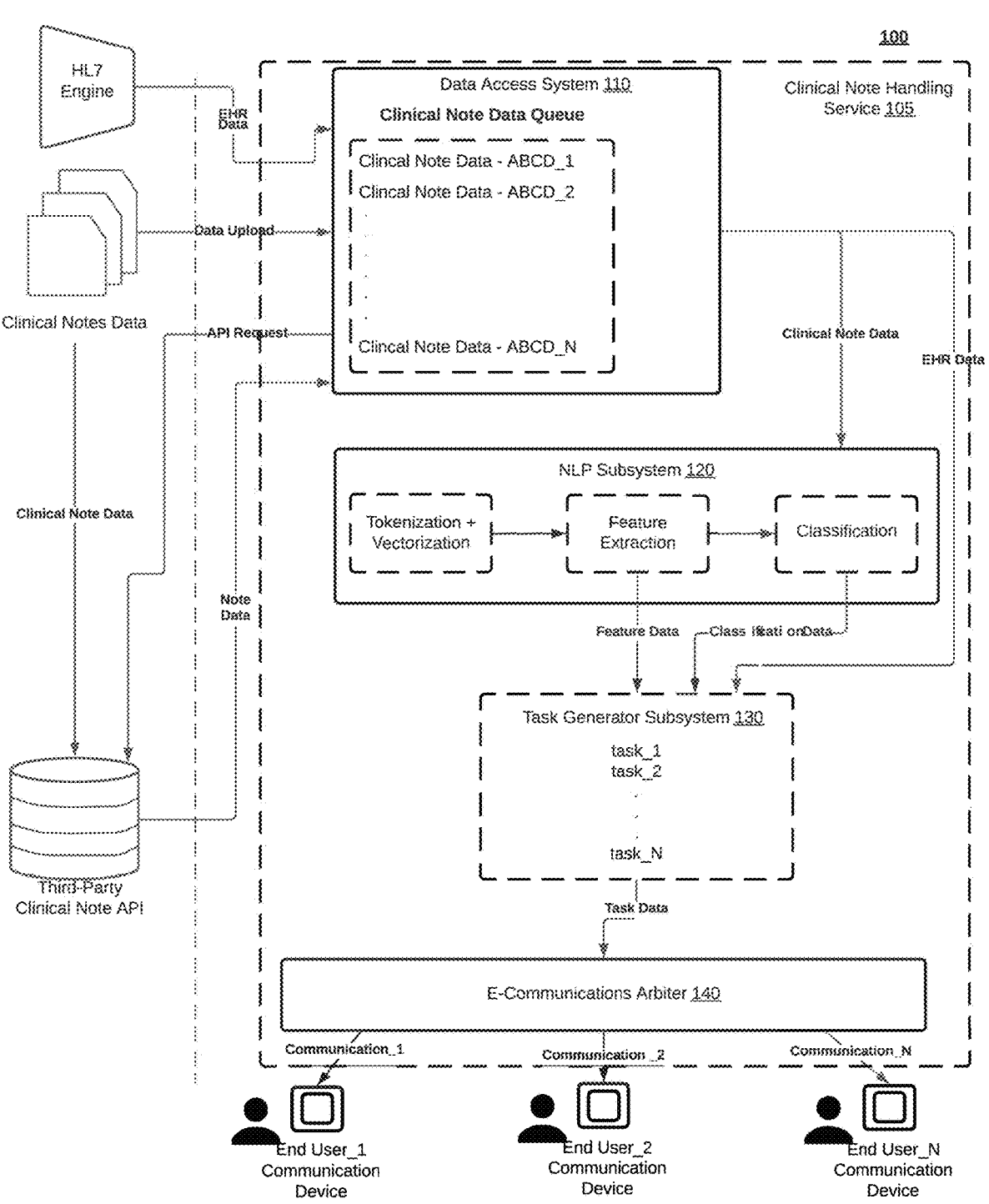
FIG. 1 illustrates a schematic representation of a system 100 in accordance with one or more embodiments of the present application.
Figure 1A:
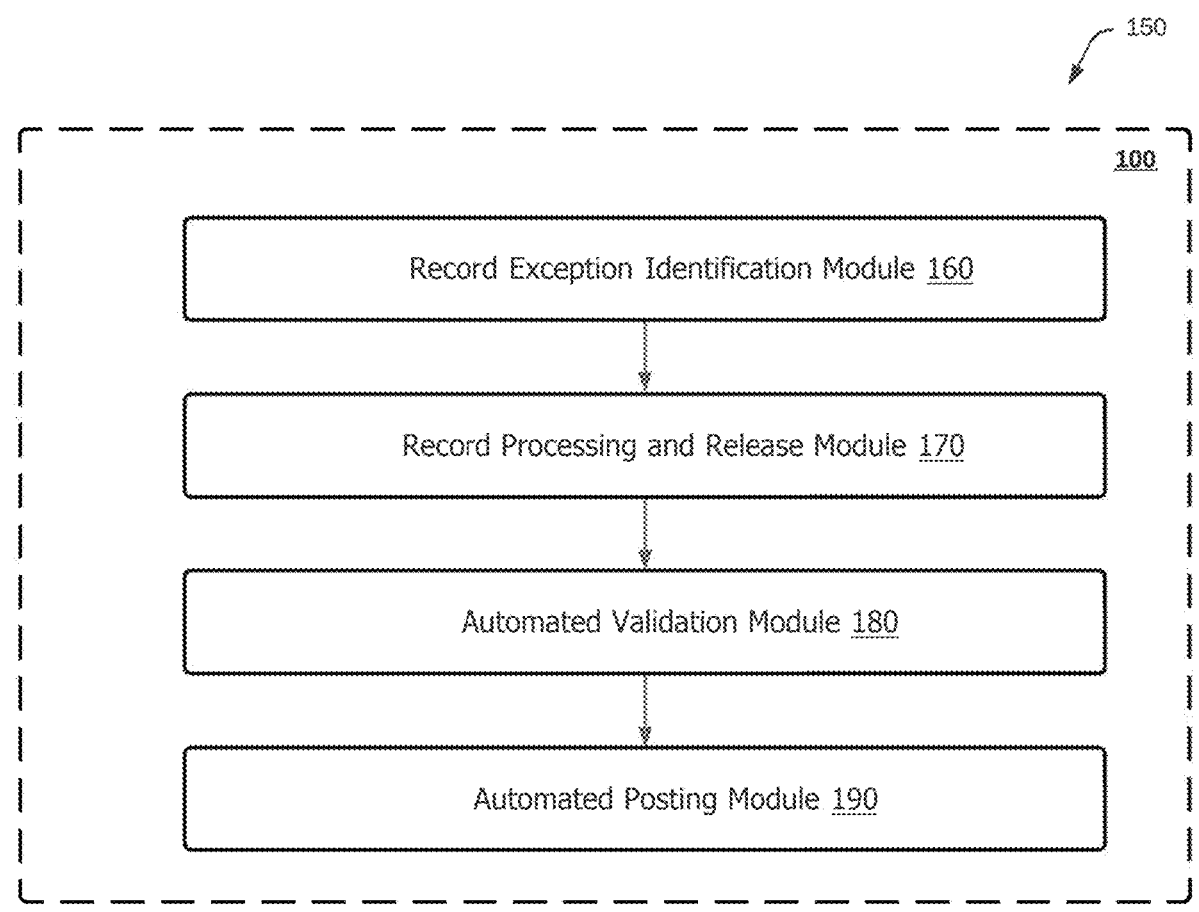
FIG. 1A illustrates a schematic representation of a subsystem 150 of the system 100 in accordance with one or more embodiments of the present application.

As shown in FIGS. 1 and 1A, a medical data processing system 100 may include a clinical note handling service 105 and a charge processing and exception handling subsystem 150. The service 105 and the subsystem 150 may each be configured to perform specific functions within the system 100 and may operate independently of or in conjunction with one another. It shall be noted that while FIGS. 1 and 1A illustrate the system 100 as including both the clinical note handling service 105 and the charge processing and exception handling subsystem 150, other embodiments of the system 100 may only include one of these two components (or include other modules not explicitly depicted in FIGS. 1 and 1A).

The clinical note handling service 105, as illustrated in FIG. 1, may include a clinical note data access and intake subsystem 110, a feature extraction and classification subsystem 120, an automated task generation subsystem 130, and an electronic communications subsystem 140. Conversely, as shown in FIG. 1A, the charge processing and exception handling subsystem 150 may include a charge exception identification module 160, a charge processing and release module 170, an automated validation module 180, and an automated posting module 190.

1.05 Clinical Note Data Handling and Automated Electronic Communications Service The clinical note data handling and automated electronic communications service 105 implementing the system 100, sometimes referred to herein as the "clinical note handling service 105" may be implemented by a distributed network of computers (e.g., hosted on the cloud, etc.) and may be in operable and control communication with each of the subsystems of the system 100 and/or third-party subsystems and services. That is, the clinical note handling service 105 may include a centralized controlling computer server(s) and associated computing systems that encourage and/or control the intelligent and accelerated clinical note data handling, clinical note data classification, and clinical note data-informed communications routing operations of each of the subsystems, described herein, (e.g., subsystems 110-140).

1.1 Clinical Note Data Access+Intake Subsystem

The clinical note data access and intake subsystem 110, which may be sometimes referred to herein as the "data access system" 110, preferably functions to enable one or more electronic connections between the system 100 and one or more external systems of one or more subscribers to the clinical note handling service 105. The data access subsystem 110 may include one or more access modules that may function to establish or create content communication channels, which are sometimes referred to as "data handling nexus", between the system 100 and systems associated with subscribers to the service 105. In one or more embodiments, the data handling nexus may include any suitable medium and/or method of transmitting digital items between at least two devices including, but not limited to, a service bus, a digital communication channel or line, and/or the like.

Additionally, or alternatively, the clinical note data access and intake subsystem 110 may provide a web-based graphical user interface or web application that may enable one or more subscribers to upload clinical note data (e.g., clinical note CSV files, and/or the like) directly into the system 100.

In one or more embodiments, based on accessing or receiving clinical note data, the data access system 110 may function to store the clinical note data in a queue and preferably generate and/or associate identifying metadata including, but not limited to, a session identifier providing a unique identification value for a clinical session associated with a target clinical note, a patient identifier, a doctor identifier, a clinical note identifier, and/or the like. In such embodiments, the identifying metadata may be passed along with the clinical note data to one or more downstream subsystems (e.g., subsystem 120, subsystem 130, subsystem 140) to enable processing, tracking, account identification, and/or the like.

In one or more embodiments, the clinical note data handling service 105 may function to implement a clinical note data handling application programming interface (API) that enables programmatic communication, access, and control between the system 100 and the one or more sub-services within the system 100 and one or more (third-party) APIs associated with one or more subscribers to the clinical note data handling service 105.

Additionally, or alternatively, the data access system 110 may receive the clinical notes data via a health level seven (HL7) interface. In such embodiments, an electronic health record (EHR) system associated with a subscriber may periodically or in real-time send one or more HL7 messages comprising clinical note data and/or other types of electronic health record (EHR) data to the data access system 110. In turn, the data access system 110 may receive the one or more HL7 messages via a secure channel (e.g., port) of the clinical note handling service 105 and provide the one or more HL7 messages to the NLP subsystem 120.

1.2 NLP: Feature Identification+Extraction and Classification Subsystem

The feature extraction and classification subsystem 120, which may sometimes be referred to herein as an "NLP subsystem", preferably functions to perform various natural language processing tasks including extracting features from clinical note data and computing one or more classification inferences and/or labels for each clinical note file being handled by the clinical note data handling service 105. The NLP subsystem 120 may additionally include one or more text processing modules and/or machine learning models that may tokenize textual data within a clinical note and vectorize and/or generate embeddings for each set of tokens and further cluster the tokens into semantically related token groups or the like.

In one or more embodiments, the NLP subsystem 120 includes a machine learning module or subsystem that may be intelligently configured to predict various classifications for each clinical note document including, but not limited to, identifying whether a clinical note has a clinical recommendation, a number of clinical recommendations in a given clinical note, a type of clinical recommendation, a strength of a clinical recommendation, an urgency of a clinical recommendation, and/or the like. In such embodiments, the NLP subsystem 120 may include a plurality of distinct machine learning-based classification submodules, which may be outlined in more detail in method 200.

Additionally, or alternatively, in some embodiments, the NLP subsystem 120 may include extensible feature extraction and classification heuristics that may be applied alone or in combination with one or more machine learning-based classifiers described herein.

Additionally, or alternatively, the NLP subsystem 120 may implement one or more ensembles of pre-trained or trained machine learning models. The one or more ensembles of machine learning models may employ any suitable machine learning including one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), adversarial learning, and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, density-based spatial clustering of applications with noise (DBSCAN), expectation maximization, etc.), a bidirectional encoder representation form transformers (BERT) for masked language model tasks and next sentence prediction tasks and the like, variations of BERT (i.e., ULMFIT, XLM UDify, MT-DNN, SpanBERT, ROBERTa, XLNet, ERNIE, KnowBERT, VideoBERT, ERNIE BERT-wwm, MobileBERT, TinyBERT, GPT, GPT-2, GPT-3, GPT-4 (and all subsequent iterations), ELMo, content2Vec, and the like), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm. Each processing portion of the system 100 can additionally or alternatively leverage: a probabilistic module, heuristic module, deterministic module, or any other suitable module leveraging any other suitable computation method, machine learning method or combination thereof. However, any suitable machine learning approach can otherwise be incorporated into the system 100. Further, any suitable model (e.g., machine learning, non-machine learning, etc.) may be implemented in the various systems and/or methods described herein.

1.3 Automated Recommendation Task Generator

The automated recommendation handling task and instructions generator 130, which may be sometimes referred to herein as a "tasks generator" 130 or "automated task generation subsystem" 130, preferably functions to automatically generate a clinical recommendation registry including one or more tasks and/or one or more instructions for handling and/or disposing of clinical recommendations identified within a clinical note. In one or more embodiments, the task generator 130 may take in as input a set of extracted features and a set of classification inferences computed by the NLP subsystem 120 to compose and/or structure a given registry. It shall be noted that, in some portions of the disclosure, a "clinical recommendation registry" may be referred to as a "clinical recommendation worklist" or the like.

A given clinical recommendation registry preferably includes an enumeration of tasks and/or computer-executable instructions that may be automatically executed by the clinical note handling service 105. Additionally, or alternatively, the clinical recommendation registry may include patient session identifier (ID) data, clinical recommendation ID data, and patient communications account data (e.g., email, phone number, messaging ID, etc.) that may be used as input in structuring one or more electronic communications to a given patient, as described herein and using at least e-communications arbiter 140.

Furthermore, in some embodiments, the task generator 130 may also be capable of ingesting additional electronic health record (EHR) data, such as appointment data, discharge data, transfer data, prescription data, and/or the like. This additional data may inform one or more operations of the task generator 130 and/or may be directly or indirectly provided as input to the e-communications arbiter 140 for structuring electronic communications to a given patient or other end users (e.g., a referring doctor, care team, etc.).

1.4 Automated E-Communications Arbiter & Routing

The electronic communications subsystem 140, which may be sometimes referred to herein as an "e-communications arbiter" 140, preferably functions to take in as input a clinical recommendation registry associated with a target clinical recommendation and structure, as output, an automated electronic communication scheme for handling and/ or disposing of the target clinical recommendation. Accordingly, the e-communications arbiter 140 may function to intelligently select an optimal communication channel for communicating with an end user or patient, structuring communication parameters, such as a communication schedule and/or communication frequency and composing message content for each communication to the end user. In one or more embodiments, the e-communication arbiter may function to employ a selection matrix or the like for selecting a most optimal communication channel and may further employ pre-trained language models and/or messaging templates to compose messaging content for a given communication.

1.5 Record Processing and Exception Handling Subsystem

The record processing and exception handling subsystem 150 may be a computer-executable software module that, when executed, performs automated record processing and exception handling for system 100. The operations and processes involved in processing and managing validated records and exceptions may be supported via one or more of the sub-modules illustrated in FIG. 1A. As illustrated in FIG. 1A, the record processing and exception handling subsystem 150 may comprise one or more submodules 160-190 that each perform distinct functions. Some of the functions performed by the submodules 160-190 will now be described below and in greater detail in method 200.

In some embodiments, the record exception identification submodule 160 may function to identify a batch of records containing exceptions and, in turn, display these records in a graphical user interface. Concurrently, the records processing and release module 170 may operate to receive user inputs for correcting the exceptions and for transitioning the records from an "exception detected" state to a "released" state. The automated validation module 180 may function to continuously monitor state changes to the records and execute one or more automated validation processes following a release of the final record in the batch. These processes may include time concurrency checks, modifier processing checks, service unit review checks, and/or the like. If no errors are detected, the submodule 180 may function to transition one or more of the records from a "released" state to a "ready to post" state. Conversely, if errors are detected in one or more of the records, the submodule 180 may automatically navigate to a directory or sub-directory containing these errors for user correction. Finally, the automated posting module 190 may function to automatically post the validated records to corresponding patient accounts. Once a record is posted, the submodule 190 may transition such record from a "validated" state to a "posted" state, indicating that the record is finalized and ready to be recorded to an insurance company or patient.

2.00 Method for Automated Batch Processing of a Plurality of Exception Records As shown in FIG. 2, a method 200 for automated batch processing of a plurality of exception records may include identifying a batch of exceptions (S210), resolving and releasing each exception record in the batch of exceptions (S220), executing automated validation for each released exception record (S230), and posting validated records (S240).

The method for automated batch processing of exception records, as described, may offer considerable technical benefits that address both intra-record and inter-record validation challenges typically encountered in data management. Data providers, particularly in specialized fields like healthcare or anesthesia, often deal with large volumes of exception records that require thorough validation for data consistency, error resolution, and cross-record dependencies. This method provides a solution that may streamline the validation process while minimizing manual review, thus reducing the likelihood of errors that can affect related records.

The automated batch processing method may significantly enhance efficiency by consolidating exception handling, validation, and resolution into a unified process. By automating intra-record and inter-record validations—including time concurrency, modifier checks, and service unit reviews—the method may proactively address discrepancies within individual records and their broader impact across other records. For example, the inter-record time concurrency validation may check for scheduling conflicts within exception records, ensuring that supervising entities are not over-assigned within a given period. Such validations, which might otherwise be complex and time-consuming to perform manually, may instead be executed automatically with each batch, reducing the overall processing time and manual intervention required.

The method implementing automated inter-record validation process may also contribute to a higher standard of data accuracy by systematically checking for and correcting discrepancies that extend beyond a single record. When validation errors are detected, the method may automatically navigate users to specific review queues for targeted correction, potentially simplifying the error resolution process. Additionally, the batch processing user interface may dynamically update to reflect resolved errors, ensuring that the validation status of each exception record is up-to-date, which may improve accuracy in tracking record progress.

Further, the method may support automated posting of validated records to user (patient) accounts once all identified errors are resolved. By enabling this automated transition from "exception detected" to "ready to post" states, the method may facilitate a seamless finalization process, further reducing the likelihood of human error and enhancing workflow efficiency. The technical advantage of reducing manual steps not only increases productivity but also minimizes the risk of oversight, supporting a more reliable record-keeping process in data management settings.

2.10 Identifying an Exception Record Batch

S210, which includes identifying an exception record batch, may function to identify an exception record batch for display within an automated batch processing graphical user interface. In general, an exception record batch may include one or more exception artifacts that have discrepancies or errors. These discrepancies or errors may be present for various reasons including, but not limited to, incorrect charge amounts, errors in patient data (e.g., user data), errors in patent visit data (e.g., user visit data), errors in artifact charge data, inconsistencies in procedure codes, incomplete or missing data, and/or the like. It shall be noted that, in some portions of the disclosure, the terms "exception record batch," "automated batch processing graphical user interface," and "charges" may alternatively be referred to as a "batch of anesthesia-related charge exceptions," an "anesthesia billing automation user interface," and "anesthesia-related charges," respectively.

Selecting an Exception Record Batch via User Input

Figure 3:
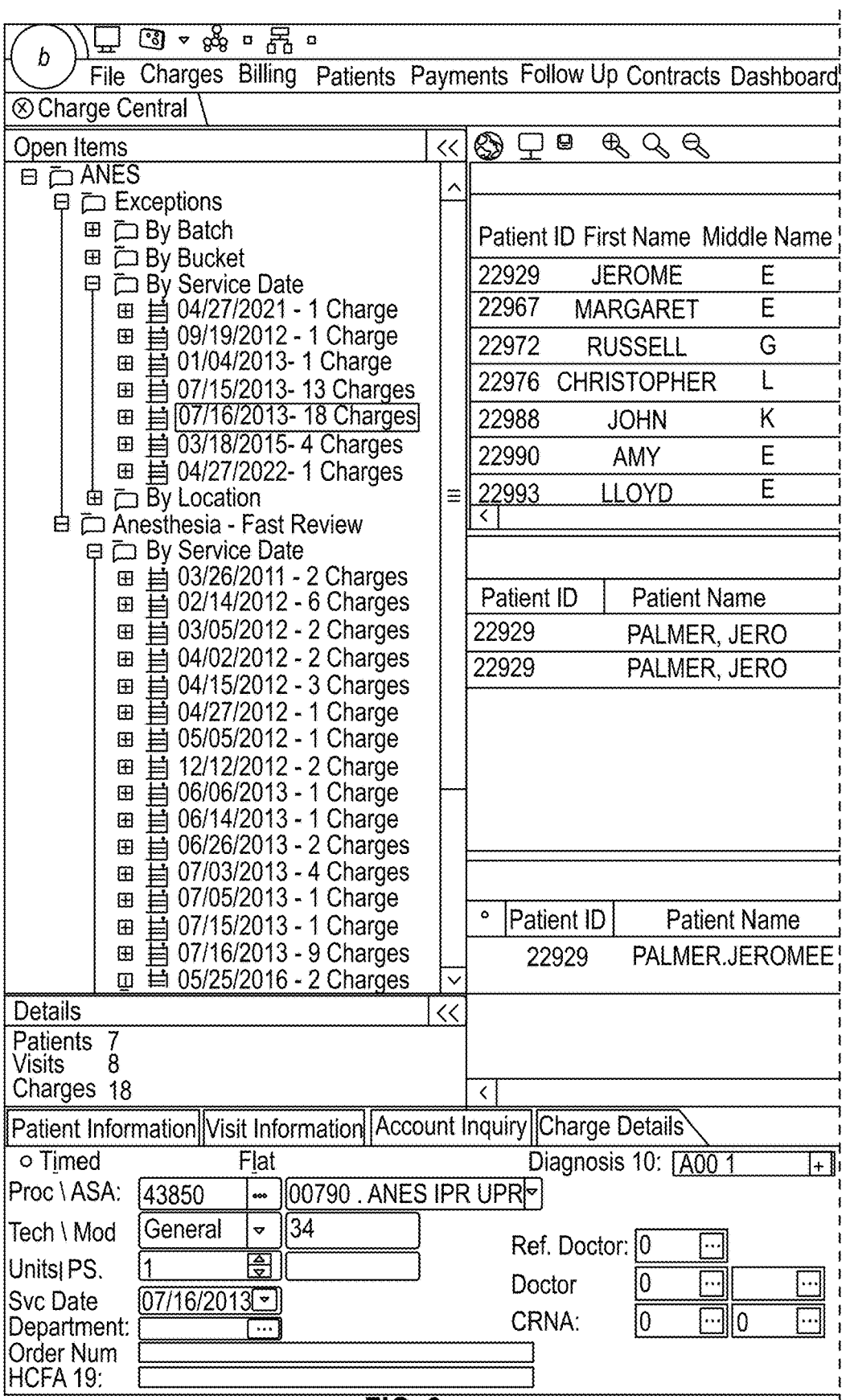
FIGS. 3-5 illustrate examples of an automated batch processing graphical user interface in accordance with one or more embodiments of the present application.

In some embodiments, an exception record batch may be identified (e.g., selected) via one or more user inputs. The one or more user inputs may include one or more navigation inputs and/or one or more selection inputs. Navigation input(s) may relate to inputs for navigating through various directories and/or sub-directories displayed within a batch explorer user interface container of the automated batch processing graphical user interface. As generally illustrated in FIG. 3, the batch explorer user interface container may include directories (e.g., parent directories, root directories, etc.) and sub-directories (e.g., sub-elements) that may be navigated via the one or more inputs. Specifically, in the example of FIG. 3, the directories and sub-directories displayed within the batch explorer user interface container may include, but should not be limited to, an "ANES" directory, an "Exceptions" sub-directory, a "By Batch" sub-directory, a "By Bucket" sub-directory, a "By Service Date" sub-directory, a "By Location" sub-directory, and/or the like.

Conversely, selection input(s) may relate to inputs that determine which exception record batch to display in the automated batch processing graphical user interface. An example of identifying an exception record batch based on the one or more navigation inputs and/or the one or more selection inputs is also illustrated in FIG. 3. Specifically, in the example illustrated in FIG. 3, S210 may receive one or more inputs for navigating to and selecting the exception record batch corresponding to the exception records related to Jul. 16, 2013. As a result, as also illustrated in FIG. 3, S210 may visually emphasize (e.g., highlight) the selected exception record batch selected in the batch explorer user interface element and concurrently display the selected exception record batch in various artifact user interface components of the automated batch processing graphical user interface, as will be described herein.

It shall be noted that the example illustrated in FIG. 3 is not intended to be limiting and that if a different batch exception record batch was selected in FIG. 3, S210 would adapt accordingly and display the different exception record batch instead.

Figure 5:
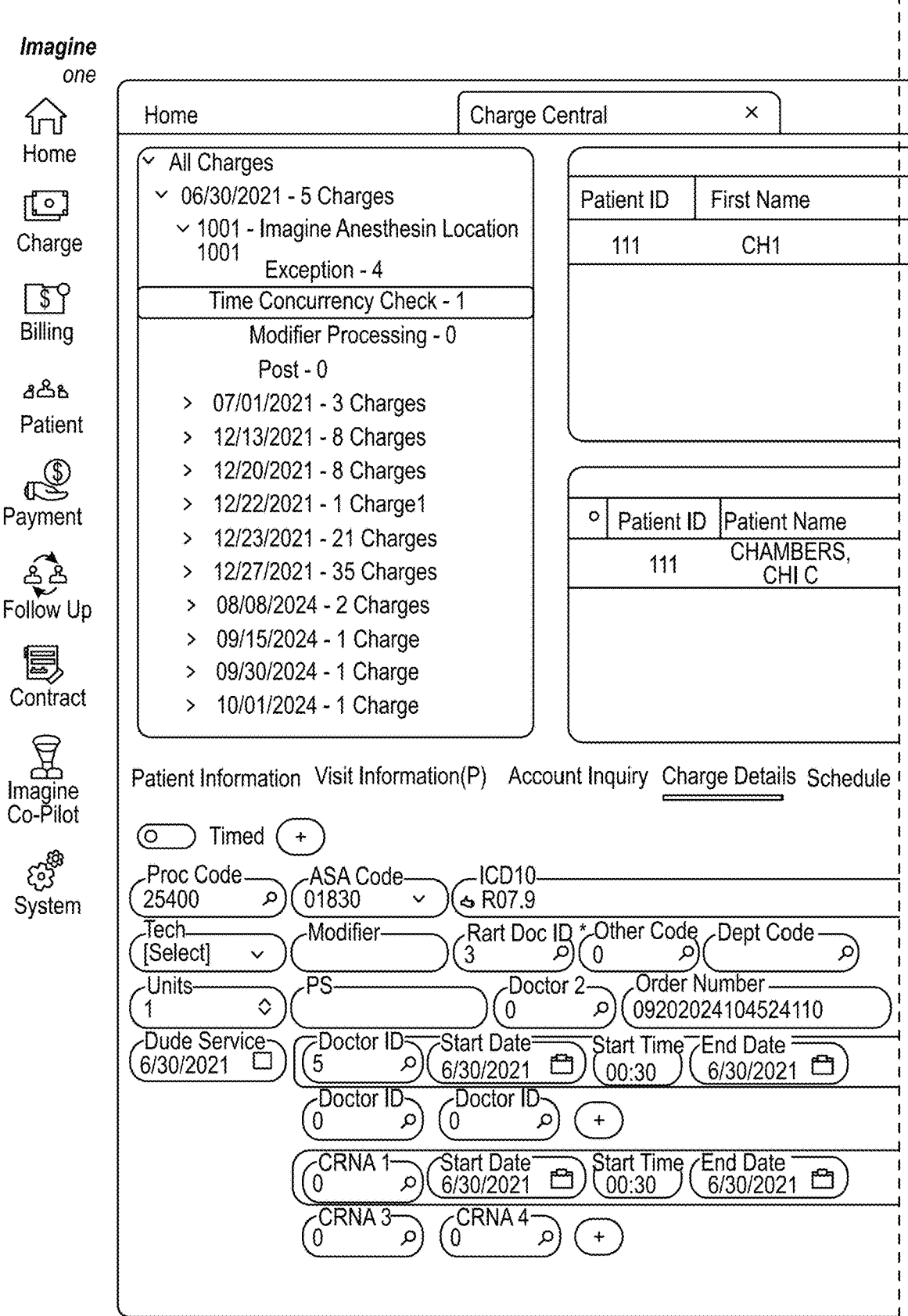

Additionally, in some embodiments, as illustrated in FIG. 5, the batch explorer user interface container may include a plurality of service period entries. A respective service period entry of the plurality of service period entries may include one or more batch node entries that correspond to one or more exception record batches associated with the respective service period entry. For example, a batch node entry may be the first batch node entry corresponding to the exception record batch selected for display.

The first batch node entry that corresponds to the exception record batch may include a plurality of sub-elements, each selectable to present different aspects of the exception record batch. A first sub-element may be selectable to display one or more groups of top-level exception records and sub-level exception records that are associated with the exception record batch. A second sub-element may be selectable to display the time concurrency review queue, which is configured to present the one or more groups of top-level exception records and sub-level exception records that are associated with the time concurrency validation error. A third sub-element may be selectable to display the modifier processing review queue, where the modifier processing review queue is configured to present the one or more groups of top-level exception records and sub-level exception records that are associated with modifier processing validation errors. A fourth sub-element may be selectable to display a post-validated records queue, which is configured to display one or more groups of top-level and sub-level validated records that are no longer associated with the time concurrency validation error or the modifier processing validation error.

Updating the Automated Batch Processing Graphical User Interface

In some embodiments, updating the automated batch processing graphical user interface in response to a selection of a respective exception record batch may include updating one or more user interface components/elements displayed within the batch processing graphical user interface (e.g., tables, grids, etc.). Specifically, in some embodiments, S210 may function to update a first, second, and/or third artifact user interface component (e.g., tables) upon detecting a selection of a respective exception record batch. The first artifact user interface component, as illustrated in FIG. 3, may include one or more rows and/or one or more columns. The one or more rows in the first artifact user interface component may each correspond to a specific entity (e.g., patient, top-level exception record, etc.) associated with the respective exception record batch, while the one or more columns in the first artifact user interface component may correspond to specific entity (e.g., patient) attributes, such as an ID of an entity, a first name of an entity, a last name of an entity, a social security number (SSN) of an entity, an address of an entity, a city associated with an entity, a state associated with an entity, a phone number associated with an entity, a date of birth of an entity, a gender of an entity, a responsible party first name associated with an entity, a responsible party last name associated with an entity, a responsible party address with an entity, and/or the like.

Conversely, as also illustrated in FIG. 3, the second artifact user interface component may include one or more rows and/or one or more columns. The one or more rows may each correspond to a visit (e.g., sub-level exception record) associated with an entity currently selected in the first artifact user interface component, whereas the one or more columns may correspond to specific attributes of a visit, such as an ID of an entity, a name of an entity, a date of birth of an entity, a visit ID or number, a visit location, a visit date, a history number, a referring doctor, a primary insurance of a patient, a secondary insurance of a patient, a tertiary insurance of a patient, a visit creation date, and/or the like. It shall be noted that the above is not intended to be limiting and that if a different top-level exception record was selected in FIG. 3, the second artifact user interface component would display sub-level exception records for the different top-level exception record.

Furthermore, as illustrated in FIG. 3, the second artifact user interface component may include one or more rows and/or one or more columns. The one or more rows may each correspond to an exception record (e.g., a secondary sub-level exception record subordinate to the sub-level exception record) associated with a visit currently selected in the first artifact user interface component, whereas the one or more columns may correspond to specific attributes of an exception record, such as an ID of an entity, a name of an entity, a number of a visit, a location of a visit, a post date, a date of service, a procedure code, a procedure code, a modifier code, a number of units, an order number, a diagnosis code, and/or the like. It shall be noted that the above is not intended to be limiting and that if a different sub-level exception record was selected in FIG. 3, the third artifact user interface component would display sub-level exception records for the different top-level exception record.

It shall also be noted that the naming used in the disclosure is not intended to be limiting. For instance, in the example illustrated in FIG. 5, the automated batch processing graphical user interface may include the second and third artifact user interface component, but not the first artifact user interface component. Accordingly, in such embodiments, the second artifact user interface component may be referred to as the "first artifact user interface component" and the records of the second artifact user interface component may be referred to as "top-level exception records." Similarly, the third artifact user interface component may be referred to as the "second artifact user interface component," and its corresponding records may be renamed to reflect their new hierarchical position (e.g., sub-level exception records).

In some embodiments, as illustrated in FIG. 5, the batch explorer user interface container, the first artifact user interface component, and the second artifact user interface component may be arranged within an upper section of the automated batch processing graphical user interface. The batch explorer user interface container may be positioned on the left side of the upper section, spanning approximately 20% of the width of the upper section, while the first artifact user interface component may be positioned on the right side, spanning about 80% of the width of the upper section. The second artifact user interface component may be arranged beneath the first artifact user interface component, similarly spanning 80% of the width.

Conversely, as also illustrated in FIG. 5, the plurality of editable user interface fields may be arranged within a lower section of the automated batch processing graphical user interface. These editable fields may be configured to receive input for modifying attributes associated with a sub-level exception record selected in the second artifact user interface component and may span the entire width of the lower section.

In analogous ways as FIG. 3, the batch explorer user interface container may further include a hierarchical view of the plurality of exception record batches. This hierarchical view may display a root node entry representing the aggregation of the exception record batches, along with batch node entries subordinate to the root node that correspond to individual exception record batches. The hierarchical view may also include additional batch node entries representing other exception record batches. Each batch node entry may include text indicating key details such as the service date associated with the exception record batch and the total number of sub-level exception records related to the top-level exception records within that batch. It shall be noted that this hierarchical structure may allow users to easily identify, review, and modify exception records, particularly when addressing validation errors or discrepancies at various levels of the batch processing workflow.

2.20 Resolving and Releasing Exceptions

S220, which includes resolving and releasing exceptions, may function to receive user input(s) for transitioning one or more exception records from an "exception detected" state to a "ready to post" state (e.g., post to a corresponding account). The user input(s) received for transitioning the one or more exception records from an "exception detected" state to a "ready to post" state may include "correction inputs" and/or "release inputs." Correction inputs, as generally referred to herein, may relate to inputs provided by the user to resolve any identified errors or discrepancies in one or more top-level and/or sub-level exception records. Conversely, release inputs may relate to inputs provided by the user to transition a respective exception record to a "ready to post" state (e.g., "released state"). The release input(s), in some embodiments, may be provided after the errors or discrepancies in an exception record have been corrected.

Displaying & Modifying Top-Level and/or Sub-Level Exception Records

In some embodiments, the automated batch processing graphical user interface may display details (e.g., attributes or properties) of a currently selected sub-level exception record. For instance, in the example illustrated in FIG. 3, the sub-level exception record of top-level exception record (e.g., the record corresponding to visit "000011640") is currently selected. As a result of detecting this selection, S220 updates the automated batch processing graphical user interface to include a detailed view of the sub-level exception record. Specifically, in the example of FIG. 3, the automated batch processing graphical user interface includes a plurality of interactive (e.g., editable) user interface fields or elements that indicate various attributes or properties of the selected sub-level exception record, such as the procedure code, the billing modifier, the number of units, the service data, the department, the order number, the diagnosis code, the referring doctor, the doctor, and the CRNA currently associated with the sub-level exception record (among others).

In some embodiments, the plurality of editable user interface fields may be configured to receive inputs for changing the attributes or properties of the currently selected sub-level exception record. The inputs may include text input, number input, selection, alphanumeric input, or any other type of input that can be used to modify the attributes or properties of a currently selected sub-level exception record. For example, as also shown in FIG. 3, the editable user interface field being displayed in associated with the label "Doctor" is displayed in an error state (e.g., highlighted in red), indicating that the current value for the "Doctor" attribute has resulted in a validation exception (e.g., is incorrect, incomplete, or does not meet specific requirements or rules set for this attribute or property). Accordingly, in this example, S220 may function to receive input(s) (e.g., "corrective inputs") for changing the "Doctor" attribute or property to a new value that resolves the validation exception. In turn, based on receiving these input(s), S220 may function to update the "Doctor" attribute to the new value provided by the user in a computer database. It shall be noted that, in some embodiments, resolving an exception associated with an attribute of a sub-level exception record may be referred to as an "intra-record" resolution process (or similar recitations), which highlights the focus on addressing issues within a single sub-level exception record, as opposed to cross-record or inter-record exception resolutions.

It shall be noted that the above example is not intended to be limiting and that additional, different, or fewer attributes or properties may be modified without departing from the scope of the disclosure. The specific attributes or properties and the types of inputs used to modify them can vary depending on the detected exceptions, specific requirements of the anesthesia billing process, the user's preferences, and/or other factors.

Releasing an Exception Record

Additionally, or alternatively, in some embodiments, S220 may function to receive one or more inputs for releasing a sub-level exception record (termed "release inputs"). A release input, in some embodiments, may include selecting a "Release" button displayed in the automated batch processing graphical user interface. For example, once the attributes and properties have been modified by the user, S220 may additionally detect a selection of the "Release" button illustrated in FIG. 3. In turn, based on the detection of this input, S220 may function to initiate or trigger a release of the sub-level exception record currently selected in the second artifact user interface component.

It shall be noted that while the above examples describe embodiments in which a charge is released upon detecting a selection of a "Release" button, other embodiments may employ different methods for releasing a charge without departing from the scope of the disclosure.

As will be described in more detail in S230, upon releasing a final sub-level exception record of the exception record batch, method 200 may automatically trigger or initiate a series of one or more automated inter-record validations (e.g., check for cascading validation errors). The automated inter-record validations may include automated time concurrency checks, automated modifier processing checks, automated charge review checks, and/or automated location checks (among others). If no errors are detected, method 200 may automatically post the validated artifacts to corresponding patient accounts. However, if inter-record errors are detected, method 200 may automatically navigate to a folder containing these errors for further correction by a user.

2.30 Executing Automated Inter-Record Validations

S230, which includes executing automated inter-record validations for sub-level exception records, may function to execute one or more inter-record validations upon detection of a trigger condition. As briefly described above, in some embodiments, the trigger condition may be the release of a final (e.g., last) sub-level exception record in the exception record batch. For instance, in a non-limiting example, if the exception record batch includes N sub-level exception records (e.g., one (1), two (2), four (4), eight (8), sixteen (16), thirty-two (32), etc.), the operations of S230 may be executed after detecting the release of the Nth sub-level exception record.

In some embodiments, the operations of S230 may be applied (and/or recursively applied) to each sub-level exception record included in the exception record batch. That is, each individual sub-level exception record in the exception record batch may be subject to the intra-record (e.g., cross-record) validation processes of S230. For instance, in a non-limiting example, consider an exception record batch that contains three sub-level exception records. Upon the release of the last sub-level exception record in the exception record batch, S230 may trigger the cross-record validation processes (e.g., inter-record validation processes). S230 may first apply these inter-record validation processes to the first sub-level exception record in the exception record batch. If any errors are detected during this validation, S230 may flag these errors and automatically navigate to a directory/folder (e.g., review queue) containing these errors for user review and correction (as described in more detail herein). Once the errors associated with the first sub-level exception record are corrected by a user, S230 may proceed to apply the validation processes to the second sub-level exception record in the batch. This process may continue, with S230 sequentially applying the validation processes to each sub-level exception record in the batch until all sub-level exception records have been validated.

Time Concurrency

In some embodiments, the plurality of inter-record validations may include an inter-record time concurrency validation. The inter-record time concurrency validation may function to verify if a supervising entity (e.g., medical professional, an anesthesiologist, doctor, etc.) is assigned to less than a threshold number of Certified Registered Nurse Anesthetists (CRNAs) (e.g., entities) in a given period. If the inter-record time concurrency validation identifies that a medical professional (e.g., supervising entity) listed on a respective artifact (e.g., sub-level exception record) is found to be supervising more than the threshold number of CRNAs, S230 may function to generate a time concurrency error signal. Alternatively, if the inter-record time concurrency validation determines that the medical professional (e.g., supervising entity) listed on the respective sub-level exception record is supervising a number of CRNAs (e.g., entities) within the acceptable threshold, S230 may generate a confirmation signal that indicates that the time concurrency check has been successfully passed and allows S230 to proceed to the next step in the validation process (e.g., if the other sub-level exceptions also do not have a time concurrency validation error).

In some embodiments, when a time concurrency error signal is generated for one or more sub-level exception records, S230 may function to re-position the one or more sub-level exception records (and associated top-level and/or secondary sub-level exception records) to a time concurrency review queue, and in turn, automatically navigate to a time concurrency folder/directory that, when selected, displays a time concurrency review queue with the one or more time concurrency errors for correction. It shall be noted that a top-level exception record associated with a time concurrency validation error, the sub-level exception records of the top-level exception record, and the secondary sub-level exception records of the sub-level exception record may be referred to as a group of exception records associated with a time concurrency validation error (e.g., a group of top-level, sub-level, and/or secondary sub-level exception records).

Figure 4:
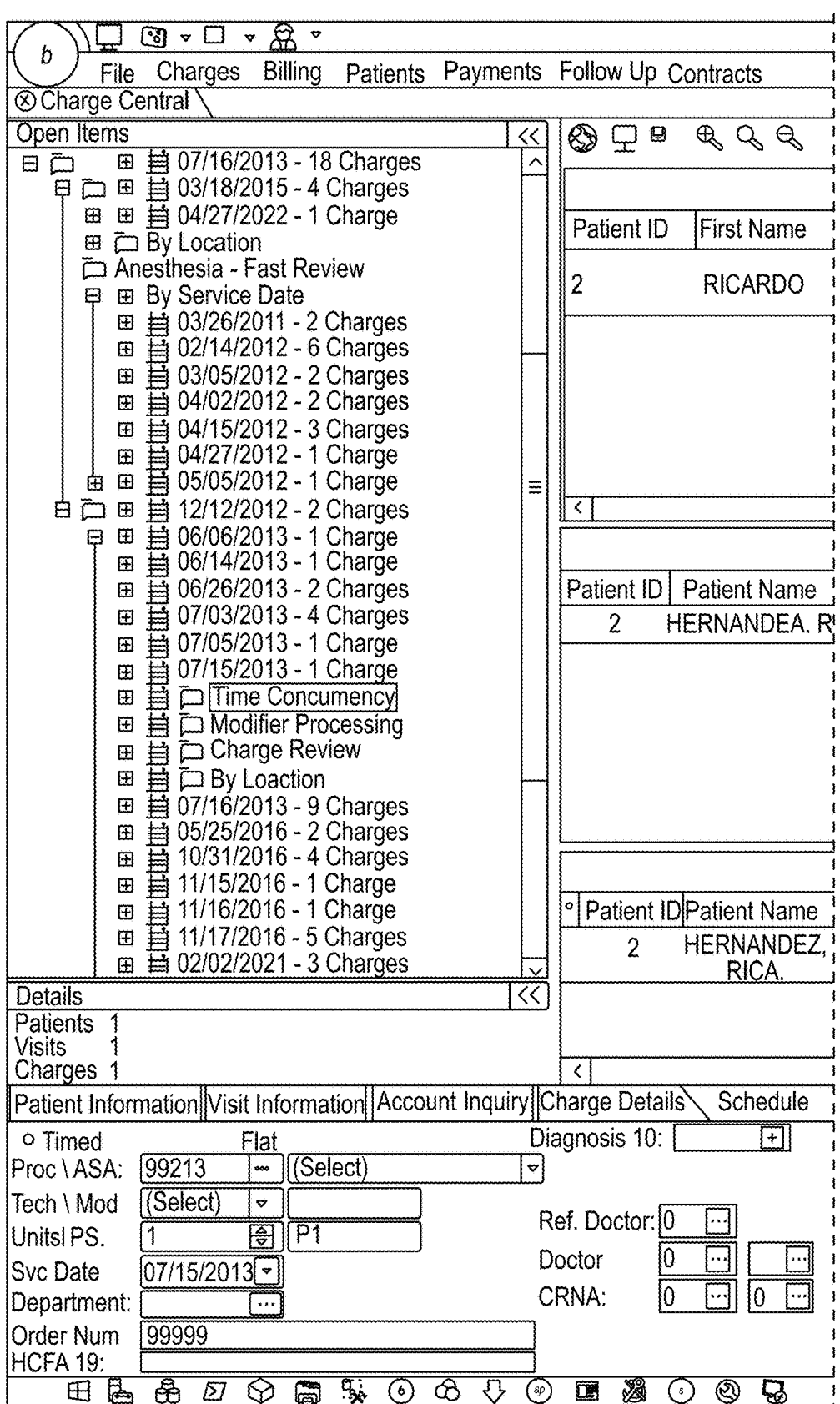

As generally illustrated, in FIG. 4, upon (automatically) navigating to the time concurrency folder/directory, the time concurrency review queue may include one or more user interface containers as described above, such as the first artifact user interface component (e.g., a patients table), the second artifact user interface component (e.g., a visits table), the third artifact user interface component (e.g., charges table), and/or the like, based on the generated time concurrency error signal(s). Specifically, as described in more detail herein, the first artifact user interface component may be updated with the top-level exception records (e.g., patients) associated with the time concurrency errors. The second artifact user interface component may be updated to display the sub-level exception records (e.g., visits) that lead to the time concurrency error(s) for the selected top-level exception record (e.g., patient). Analogously, the third artifact user interface component may be updated to reflect the second sub-level exception records (e.g., charges) that lead to the time concurrency error(s) for a selected sub-level exception record.

It shall be noted that the naming used in the disclosure is not intended to be limiting. For instance, in one or more other embodiments, the time concurrency review queue may include the second and third artifact user interface component, but not the first artifact user interface component. Accordingly, in such embodiments, the second artifact user interface component may be referred to as the "first artifact user interface component" and the records of the second artifact user interface component may be referred to as "top-level exception records." Similarly, the third artifact user interface component may be referred to as the "second artifact user interface component," and its corresponding records may be renamed to reflect their new hierarchical position (e.g., sub-level exception records).

It shall also be noted that, in some embodiments, a top-level exception record is considered to be associated with a time concurrency error when a secondary sub-level exception record related to a respective patient's service (e.g., anesthesia service) triggers a time concurrency error. Similarly, in some embodiments, a sub-level exception record (e.g., visit record) is considered to be associated with a time concurrency error when the secondary sub-level exception record generated from a corresponding visit resulted in one or more time concurrency errors. Lastly, it shall be noted that, in some embodiments, a secondary sub-level exception record is associated with a time concurrency error when the attributes of that exception record (e.g., such as the responsible doctor field or the like) resulted in one or more time concurrency errors.

In some embodiments, once a specific top-level exception record associated with a time concurrency error is selected, S230 may update the second artifact user interface component to include the sub-level exception records pertaining to the specific top-level exception record that led to the time concurrency error. As described previously in S210, each sub-level exception record of the second artifact user interface component may be represented as a distinct row that includes various visit attributes/details, such as the ID of the entity associated with the sub-level exception record (e.g., visit), the name of the entity associated with the sub-level exception record, the date of birth of the entity associated with the sub-level exception record, the visit ID or number associated with the sub-level exception record, the location of the visit, the date of the visit, the history number associated with the sub-level exception record, the referring doctor for the visit, the primary, secondary, or tertiary insurance associated with the sub-level exception record, and/or the like.

Analogously, in some embodiments, upon S230 detecting a selection of a specific sub-level exception record in the second artifact user interface component (e.g., visits table), S230 may update the third artifact user interface component to include the secondary sub-level exception records (e.g., charges) pertaining to the specific sub-level exception record that led to the time concurrency error. As previously described in S210, each secondary sub-level exception record in the third artifact user interface component may be represented as a distinct row that includes various attributes/details such as the ID of an entity associated with the secondary sub-level exception record, the name of the entity associated with the secondary sub-level exception record, the ID or number associated with the visit, the location of the visit, the post date for the secondary sub-level exception record, the date of service associated with the secondary sub-level exception record, the procedure associated with the secondary sub-level exception record, the billing procedure associated with the secondary sub-level exception record, the modifier associated with the secondary sub-level exception record, the number of units associated with the secondary sub-level exception record, the order number associated with the secondary sub-level exception record, the diagnosis code(s) associated with the secondary sub-level exception record, and/or the like.

It shall further be noted that, in some embodiments, a top-level exception record, any associated sub-level exception records, and/or any associated secondary sub-level exception records detected via the inter-record time concurrency validation may be collectively referred to as a group of exception records that are collectively associated with a time concurrency validation error (e.g., a group of top-level, sub-level, and/or secondary sub-level exception records). Accordingly, in some embodiments, with reference to the above-described embodiments, S230 may function to automatically re-position the one or more groups of top-level, sub-level, and/or secondary sub-level exception records associated with a time concurrency validation error into a time concurrency review queue (of or associated with the batch explorer user interface element).

Furthermore, as also illustrated in FIG. 4, upon detecting a selection of a specific secondary sub-level exception record in the third artifact user interface component, S230 may display a record details user interface. The records details user interface, as illustrated in FIG. 4, may include a plurality of editable user interface input elements or fields that are configured to receive input for correcting attribute or property errors that lead to the time concurrency error(s) for the selected secondary sub-level exception record. After receiving the user input for correcting the time concurrency errors, S230 may function to apply the corrections to the selected secondary sub-level exception record. This may involve updating the secondary sub-level exception record attributes in a computer database, re-calculating the time concurrency based on the corrected attributes, re-checking for any remaining errors across a remainder of the secondary sub-level exception records, and/or the like.

If the corrected attributes resolve the time concurrency error(s) (e.g., optionally after all other time concurrency errors associated with other secondary sub-level exception records), S230 may cease displaying the one or more groups of top-level exception records previously associated with the time concurrency validation error in the time concurrency review queue, and proceed to the next step in the inter-record automated validation process, such as modifier validation or the like. Conversely, if time concurrency errors still exist among the secondary sub-level exception records associated with an exception record batch, S230 may forgo the next step in the inter-record automated validation process until no such error exists, and instead present the user with the record details user interface, allowing the user to make further corrections. This iterative process ensures that all time concurrency errors are addressed before the secondary sub-level exception records are posted.

Modifier Processing

In some embodiments, the inter-record validation processes of S230 may additionally or alternatively include an inter-record modifier validation process. The inter-record modifier validation process, in some embodiments, may be initiated or executed after the completion of the inter-record time concurrency validation. Additionally, or alternatively, in some embodiments, the inter-record modifier validation process may function to check the modifiers defined for each secondary sub-level exception record in the exception record batch against predefined modifier rules. Modifiers, as used herein, may refer to (medical) codes that classify an associated medical service or charge. For instance, the medical billing modifiers may denote information such as whether multiple procedures were performed during a same visit or session, if a procedure was performed by more than one medical professional, if a procedure was performed more than once, the type of services/procedures performed, the diagnosis of a patient, and/or the like.

In some embodiments, the inter-record modifier validation process may function to check the completeness of the modifiers specified in a secondary sub-level exception record. This particular check may ensure that all required modifiers have been provided for each secondary sub-level exception record in the exception record batch. For instance, a respective secondary sub-level exception record may define a number of mandatory modifiers (e.g., diagnosis modifiers, procedure modifiers, and/or the like). However, if a respective secondary sub-level exception record does not include all the mandatory modifiers (e.g., some modifiers are missing, incomplete, or not provided by the user), the inter-record modifier validation process may function to generate an error signal for the respective secondary sub-level exception record indicating such validation errors. Conversely, if the respective secondary sub-level exception record does include all the mandatory modifiers, the modifier validation process may function to generate a confirmation signal for the respective charge indicating a successful validation.

Additionally, or alternatively, the inter-record modifier validation process may check the correctness of the modifiers specified in a secondary sub-level exception record. This particular check may ensure that the modifiers applied to a secondary sub-level exception record are consistent with information included in each secondary sub-level exception record in the exception record batch, such as the diagnosis and procedure codes. For instance, a modifier denoting that a procedure was performed by more than one medical professional may be inconsistent with a procedure code that denotes a procedure that is typically performed by a single medical professional. If such an inconsistency is detected, the modifier validation process may function to generate an error signal for the respective charge indicating such validation errors. Conversely, if the respective charge does include all the mandatory modifiers, the modifier validation process may function to generate a confirmation signal for the respective secondary sub-level exception record indicating a successful validation.

It shall be noted that, when errors are detected, S230 may function to re-position the one or more (secondary) sub-level exception records (and associated top-level and/or (secondary) sub-level exception records) to a modifier processing review queue and, in turn may automatically navigate to and present a respective folder/directory (e.g., a modifier processing folder) containing such errors in a similar manner as described above. It shall also be noted that this automatic navigation and presentation of errors may streamline the correction process by reducing the number of steps the user has to take to locate and correct the errors. It shall further be noted that a top-level exception record associated with a modifier processing validation error, the sub-level exception records of the top-level exception record, and the secondary sub-level exception records of the sub-level exception record may be referred to as a group of exception records associated with a modifier processing validation error (e.g., a group of top-level, sub-level, and/or secondary sub-level exception records).

Accordingly, in analogous ways as described above, if S230 receives inputs that corrects the modifier processing validation error(s) (e.g., optionally after all other modifier processing validation error(s) associated with other secondary sub-level exception records), S230 may cease displaying the one or more groups of top-level exception records previously associated with the modifier processing validation error(s) in the modifier processing review queue, and proceed to the next step in the inter-record automated validation process, such as service unit review or the like. Conversely, if modifier processing validation error(s) still exist among the secondary sub-level exception records associated with an exception record batch, S230 may forgo the next step in the inter-record automated validation process until no such error exists, and instead present the user with the record details user interface, allowing the user to make further corrections. This iterative process ensures that all modifier processing validation error(s) are addressed before the secondary sub-level exception records are posted.

It shall also be noted that, in some embodiments, a top-level exception record, any associated sub-level exception records, and/or any associated secondary sub-level exception records detected via the inter-record modifier validation may be collectively referred to as a group of exception records that are collectively associated with a modifier processing validation error (e.g., a group of top-level, sub-level, and/or secondary sub-level exception records). Accordingly, in some embodiments, with reference to the above-described embodiments, S230 may function to automatically re-position the one or more groups of top-level, sub-level, and/or secondary sub-level exception records associated with a modifier processing validation error into a modifier processing review queue (of or associated with the batch explorer user interface element).

Service Unit Review

In some embodiments, the inter-record validation processes of S230 may include an inter-record service unit review validation process. The inter-record charge service unit review validation process, in some embodiments, may be initiated or executed following the completion of the inter-record modifier validation processing (e.g., for all secondary sub-level exception records). Additionally, or alternatively, in some embodiments, the inter-record service unit review validation process may function to validate the service specified in each secondary sub-level exception record in the exception record batch. Specifically, in some examples, validating the service specified in each secondary sub-level exception record may include validating the time-based units specified in each secondary sub-level exception record. Time-based units, as generally used herein, may relate to a standardized measure of the duration of a medical procedure or service. For instance, in a non-limiting example, if a procedure or service lasts for an hour, the associated charge may specify four (4) units.

In some embodiments, the inter-record service unit review validation process may function to check compliance with specific recording requirements of medical (e.g., anesthesia) services. This may aid method 200 in ensuring that the time-based units specified in each secondary sub-level exception do not exceed the maximum limit set for specific procedures associated with such services. For instance, a specific procedure (e.g., epidurals, surgeries, and/or the like) may define a maximum limit of time units that can be performed (e.g., recorded). However, if a respective secondary sub-level exception record exceeds this maximum limit (e.g., the time units recorded are more than the allowed limit), the inter-record service unit review validation process may function to generate an error signal for the respective secondary sub-level exception record indicating such validation errors. Conversely, if the respective secondary sub-level exception record does not exceed the maximum limit, the inter-record service unit review validation process may function to generate a confirmation signal for the respective secondary sub-level exception record indicating a successful validation.

It shall be noted that, when errors are detected for one or more secondary sub-level exception records, S230 may automatically navigate to and present a respective folder/directory (e.g., a charge or service unit review folder) containing such errors in a similar manner as described above.

2.40 Automated Posting of Validated Records

S240, which includes posting validated records, may function to automatically post the validated records to corresponding patient accounts. Upon S240 posting a respective validated record to a patient account, the respective validated record may be transitioned from a "validated" state to a "posted" state. As generally referred to herein, a validated record in a "posted" state may indicate or signify that the record previously associated with an exception is finalized and ready to be recorded to an external entity (e.g., insurance company) or patient (if appropriate).

For instance, in scenarios where method 200 receives secondary sub-level exception records for multiple patients, S230—described above—may function to automatically execute processes for validating the secondary sub-level exception records including time concurrency, modifier processing, service unit review, and/or the like. Upon S230 determining that all errors detected by the validation processes have been corrected (or determining that no errors existed), S240 may function to automatically convert these secondary sub-level exception records previously associated with a time concurrency validation error, modifier processing validation error, service unit validation error and/or the like to validated records, post these converted validated records to corresponding patient accounts, and transition these validated records from a "validated" state to a "posted" state once successfully posted to the patient accounts. It shall be noted that this conversation, transition of states, and posting of charges to patient accounts may occur without any additional user input. This means that once method 200 has received user input for releasing the secondary sub-level exception records, the operations of S240 may be automatically initiated and performed without user input, thereby reducing manual steps and the potential for human error.

In a variation of S240, in some embodiments, a validated record may be posted upon (e.g., in response to) receiving a user input within a post-validated records queue. For instance, S240 may function to post a validated record upon receiving a user input selecting a 'Post' or 'Release' button while such a record is selected in a post-validated record queue (similar to the review queues described above). In turn, based on detecting the user input selecting the 'Post' or 'Release' button, S240 may additionally function to perform similar or analogous processes described above.

It shall be noted that while the above example describes posting a validated record via a selectable button, other methods of initiating the posting process may additionally or alternatively be implemented without departing from the scope of the disclosure. It shall also be noted that a top-level validated record that is not associated with an exception, the sub-level validated records associated with top-level validated record, and the secondary sub-level validated records of the sub-level validated record may be referred to as a group of validated records (e.g., a group of top-level, sub-level, and/or secondary sub-level validated records).

3. Computer-Implemented Method and Computer Program Product

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

The system and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processors and/or the controllers. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application-specific processor, but any suitable dedicated hardware or hardware/firmware combination device can alternatively or additionally execute the instructions.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer-readable medium claims where the system or computer-readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that similar to a method with contingent steps, a system or computer-readable storage medium can repeat the steps of a method as many times as are needed to ensure that all of the contingent steps have been performed.

Although omitted for conciseness, the preferred embodiments include every combination and permutation of the implementations of the systems and methods described herein.

As a person skilled in the art will recognize from the previous detailed description and the figures and claims, modifications and changes can be made to the preferred embodiments of the invention without departing from the scope of this invention defined in the following claims.

I claim:
1. A method comprising:
in response to detecting a trigger condition via an automated batch processing graphical user interface, automatically executing a plurality of inter-record validations for an exception record batch, including:
(I) automatically generating, via an inter-record time concurrency validation, a time concurrency error signal indicating that one or more first groups of top-level exception records and sub-level exception records of the exception record batch is associated with a time concurrency validation error,
(II) automatically re-positioning the one or more first groups of top-level exception records and sub-level exception records associated with the time concurrency validation error into a time concurrency review queue of the automated batch processing graphical user interface based on the automatically generating of (I), (III) automatically generating, via an inter-record modifier validation, a modifier processing error signal indicating that one or more second groups of top-level exception records and sub-level exception records of the exception record batch is associated with a modifier processing validation error, and (IV) automatically re-positioning the one or more second groups of top-level exception records and sub-level exception records associated with the modifier processing validation error into a modifier process- ing review queue of the automated batch processing graphical user interface based on the automatically generating of (III); and executing automated navigation within the automated batch processing graphical user interface in response to the plurality of inter-record validations automatically detecting one or more inter-record errors, including the time concurrency validation error and the modifier processing validation error.

2. The method according to claim 1, wherein automated batch processing graphical user interface comprises: a batch explorer user interface container that includes a hierarchical view of a plurality of exception record batches, a first artifact user interface component that is configured to display a plurality of top-level exception records associated with the exception record batch selected in the batch explorer user interface container, a second artifact user interface component that is config- ured to display a plurality of sub-level exception records subordinate to a top-level exception record selected in the first artifact user interface component, and a plurality of editable user interface fields that are con- figured to receive input for modifying a plurality of attributes associated with a sub-level exception record selected in the second artifact user interface compo- nent.

3. The method according to claim 2, further comprising: receiving, via the plurality of editable user interface fields, one or more inputs for intra-record resolution of an attribute exception associated with one or more attri- butes of the plurality of attributes associated with the sub-level exception record.

4. The method according to claim 3, further comprising: after re-positioning the one or more first groups of top-level exception records and sub-level exception records into the time concurrency review queue:

receiving, via the automated batch processing graphical user interface, one or more inputs for resolving the time concurrency validation error associated with the one or more first groups of top-level exception records and sub-level exception records, and in response to receiving the one or more inputs for resolving the time concurrency validation error:

ceasing display of the one or more first groups of top-level exception records and sub-level excep- tion records previously associated with the time concurrency validation error in the time concur- rency review queue; and automatically executing the inter-record modifier validation after resolving the time concurrency validation error.

5. The method according to claim 4, wherein:

the time concurrency validation error is caused by a violation of a value of an attribute being concurrently assigned to more than a pre-defined number of sub- level exception records during a respective time inter- val, and the one or more inputs for resolving the time concurrency validation error modifies the value of the attribute across the one or more first groups of top-level excep- tion records and sub-level exception records to satisfy the pre-defined number.

6. The method according to claim 3, further comprising: after re-positioning the one or more second groups of top-level exception records and sub-level exception records into the modifier processing review queue:

receiving, via the automated batch processing graphical user interface, one or more inputs for resolving the modifier processing validation error associated with the one or more second groups of top-level exception records and sub-level exception records, and in response to receiving the one or more inputs for resolving the modifier processing validation error:

ceasing display of the one or more second groups of top-level exception records and sub-level excep- tion records previously associated with the modi- fier processing validation error in the modifier processing review queue;

converting the one or more second groups of top- level exception records and sub-level exception records previously associated with the modifier processing validation error to one or more groups of top-level and sub-level validated records; and automatically moving the one or more groups of top-level and sub-level validated records into a post-validated records queue for transmitting to one or more corresponding user accounts.

7. The method according to claim 6, wherein:

the modifier processing validation error is caused by a violation of a modifier attribute applied to one or more sub-level exception records of the one or more second groups of top-level exception records and sub-level exception records that conflicts with predefined modi- fier rules.

8. The method according to claim 3, wherein:

the attribute exception associated with the one or more attributes includes a respective attribute of the plurality of attributes having an incorrect value, the one or more inputs for intra-record resolution of the attribute exception include an input for modifying the respective attribute from having the incorrect value to having a correct value, and the plurality of inter-record validations determines if changing the respective attribute to the correct value results in any cascading validation errors across other top-level exception records or other sub-level excep- tion records of the exception record batch.

9. The method according to claim 3, wherein:

the batch explorer user interface container includes a plurality of service period entries, and a respective service period entry of the plurality of service period entries includes one or more batch node entries that corresponds to one or more exception record batches associated with the respective service period entry, including a first batch node entry corresponding to the exception record batch; and the first batch node entry that corresponds to the exception record batch includes a plurality of sub-elements, including:

a first sub-element that is selectable to display one or more groups of top-level exception records and sub-level exception records that are associated with the exception record batch;

a second sub-element that is selectable to display the time concurrency review queue, wherein the time concurrency review queue is configured to present the one or more first groups of top-level exception records and sub-level exception records that are associated with the time concurrency validation error;

a third sub-element that is selectable to display the modifier processing review queue, wherein the modifier processing review queue is configured to present the one or more second groups of top-level exception records and sub-level exception records that are associated with modifier processing validation error; and a fourth sub-element that is selectable to display a post-validated records queue, wherein the post-validated records queue is configured to display one or more groups of top-level and sub-level validated records that are no longer associated with the time concurrency validation error and the modifier processing validation error.

10. The method according to claim 3, wherein:

the sub-level exception record corresponds to an unreleased sub-level exception record, a respective editable user interface field is visually emphasized to indicate that a value of a respective attribute of the plurality of attributes relates to the attribute exception, the one or more inputs include a first input for changing the value of the respective attribute to a new value that resolves the attribute exception, and the method further comprises:

receiving, via the automated batch processing graphical user interface, a second input for releasing the unreleased sub-level exception record with the new value for the respective attribute, and based on receiving the first input and the second input:

converting, in a computer database, the unreleased sub-level exception record to a released sub-level exception record;

determining if the exception record batch includes another unreleased sub-level exception record; and if the determining determines that the exception record batch does includes another unreleased sub-level exception record:

automatically executing the plurality of inter-record validations for each remaining unreleased sub-level exception record in the exception record batch.

11. The method according to claim 10, wherein:

the method further comprises:

based on receiving the first input and the second input:

if the determining determines that the exception record batch does not include another unreleased sub-level exception record:

forgoing automatically executing the plurality of inter-record validations until the exception record batch does not include another unreleased sub-level exception record.

12. The method according to claim 3, wherein a respective editable user interface field of the plurality of editable user interface elements:

corresponds to a respective attribute of the plurality of attributes associated with the sub-level exception record, includes a value of the respective attribute in the sub-level exception record, and is visually emphasized to indicate that the value of the respective attribute relates to an exception.

13. The method according to claim 3, wherein:

a first sub-level exception record of the plurality of sub-level exception records corresponds to the sub-level exception record selected in the second artifact user interface component, and the method further comprises:

receiving an input for changing the sub-level exception record selected in the second artifact user interface component from the first sub-level exception record to a second sub-level exception record of the plurality of sub-level exception records; and updating the plurality of editable user interface fields from modifying the plurality of attributes associated with the first sub-level exception record to modifying the plurality of attributes associated with the second sub-level exception record.

14. The method according to claim 13, wherein:

when the sub-level exception record selected in the second artifact user interface component corresponds to the first sub-level exception record, the plurality of editable user interface fields display values of the plurality of attributes associated with the first sub-level exception record; and when the sub-level exception record selected in the second artifact user interface component corresponds to the second sub-level exception record, the plurality of editable user interface fields display values of the plurality of attributes associated with the second sub-level exception record.

15. The method according to claim 3, wherein:

the automated batch processing graphical user interface includes an upper section and a lower section;

the upper section of the automated batch processing graphical user interface includes:

the batch explorer user interface container positioned on a left side of the upper section, wherein the batch explorer user interface container spans 20% of a width of the upper section, the first artifact user interface component positioned on a right side of the upper section, wherein the first artifact user interface component spans 80% of the width of the upper section, and the second artifact user interface component positioned on the right side of the upper section and below the first artifact user interface component, wherein the second artifact user interface component spans 80% of the width of the upper section; and the lower section of the automated batch processing graphical user interface includes:

the plurality of editable user interface fields that are configured to receive the input for modifying the plurality of attributes associated with the sub-level exception record selected in the second artifact user interface component, wherein the plurality of editable user interface fields spans 100% of a width of the lower section.

16. The method according to claim 3, further comprising:

receiving, via the batch explorer user interface container, an input selecting a batch node entry corresponding to the exception record batch; and based on receiving the input selecting the batch node entry:

obtaining, from a computer database, the plurality of top-level exception records associated with the exception record batch; and displaying the plurality of top-level exception records in the first artifact user interface component based on the obtaining of the plurality of top-level exception records;

receiving, via the first artifact user interface component, a second input selecting an entry corresponding to the top-level exception record of the plurality of top-level exception records; and based on receiving the second input:

obtaining, from the computer database, the plurality of sub-level exception records subordinate to the top-level exception record; and displaying the plurality of sub-level exception records in the second artifact user interface component based on the obtaining of the plurality of sub-level exception records.

17. The method according to claim 3, wherein the hierarchical view of the plurality of exception record batches includes:

a root node entry that represents an aggregation of the plurality of exception record batches, a batch node entry that is subordinate to the root node entry and corresponds to the exception record batch of the plurality of exception record batches, and a plurality of additional batch node entries that correspond to other exception record batches in the plurality of exception record batches.

18. The method according to claim 17, wherein the batch node entry corresponding to the exception record batch includes text that indicates:

a service date associated with the exception record batch, and a total number of sub-level exceptions subordinate to the plurality of top-level exception records.

19. The method according to claim 3, wherein:

a first top-level exception record of the plurality of top-level exception records corresponds to the top-level exception record selected in the first artifact user interface component, and the method further comprises:

receiving an input for changing the top-level exception record selected in the first artifact user interface component from the first top-level exception record to a second top-level exception record of the plurality of top-level exception records; and updating the second artifact user interface component from displaying the plurality of sub-level exception records subordinate to the first top-level exception record to displaying a plurality of sub-level exception records subordinate to the second top-level exception record.

20. A method comprising:

receiving, via a plurality of editable user interface fields, one or more inputs for intra-record resolution of an attribute exception associated with a first sub-level exception record;

automatically executing a plurality of recursive inter-record validations, wherein automatically executing the plurality of recursive inter-record validations at least includes:

automatically re-positioning one or more first groups of top-level exception records and sub-level exception records associated with a time concurrency validation error into a time concurrency review queue, and automatically re-positioning one or more second groups of top-level exception records and sub-level exception records associated with a modifier processing validation error into a modifier processing review queue;

automatically detecting, via the plurality of recursive inter-record validations, that the one or more first inputs for intra-record resolution of the first sub-level exception record have caused one or more inter-record errors among the first sub-level exception record and one or more second sub-level exception records, including the time concurrency validation error and the modifier processing validation error; and executing automated navigation within the automated batch processing graphical user interface in response to automatically detecting the one or more inter-record errors.

* * * * *